(12) United States Patent
Podhajcer et al.

(10) Patent No.: US 8,436,160 B2
(45) Date of Patent: May 7, 2013

(54) ISOLATED DNA FRAGMENT OF THE SPARC HUMAN PROMOTER AND ITS USE FOR DRIVING THE EXPRESSION OF AN HETEROLOGOUS GENE IN TUMOR CELLS

(75) Inventors: Osvaldo Luis Podhajcer, Buenos Aires (AR); Eduardo Gustavo Alfredo Cafferata, Buenos Aires (AR); Maria Veronica Lopez, La Plata (AR); Diego Luis Viale, Buenos Aires (AR)

(73) Assignees: Consejo Nacional de Investigaciones Cientificas y Tecnicas (Conicet), Buenos Aires (AG); Fundacion Instituto Leloir, Buenos Aires (AG)

( * ) Notice: Subject to any disclaimer, the term of this patent is extended or adjusted under 35 U.S.C. 154(b) by 892 days.

(21) Appl. No.: 12/298,743

(22) PCT Filed: Apr. 26, 2007

(86) PCT No.: PCT/US2007/010196
§ 371 (c)(1),
(2), (4) Date: Mar. 2, 2009

(87) PCT Pub. No.: WO2007/127347
PCT Pub. Date: Nov. 8, 2007

(65) Prior Publication Data
US 2009/0312401 A1 Dec. 17, 2009

(30) Foreign Application Priority Data
Apr. 28, 2006 (AR) .................................. P060101724

(51) Int. Cl.
*C07H 21/02* (2006.01)
*C12N 15/00* (2006.01)
*A61K 48/00* (2006.01)

(52) U.S. Cl.
USPC ...................................... 536/24.1; 435/320.1

(58) Field of Classification Search .................. None
See application file for complete search history.

(56) References Cited

U.S. PATENT DOCUMENTS 6,159,467 A * 12/2000 Chung et al. .................. 424/93.6
6,596,534 B1 * 7/2003 Chung et al. ............... 435/320.1

FOREIGN PATENT DOCUMENTS

| WO | WO 00/72679 | 12/2000 |
| WO | WO 2005/017183 | 2/2005 |
| WO | WO 2007/127347 | 11/2007 |

OTHER PUBLICATIONS

Hafner et al. A Purine-rich sequence in the human BM-40 gene promoter region is a prerequisite for maximum transcription. Matrix Biology 14:733-741, 1994.*
Matsubara S et al. A conditional replciation-competent adenoviral vector, Ad-OC-E1a, to cotarget prostate cancer and bone stroma in an experimental model of androgen-independent prostate cancer bone metastasis. Cancer Res. 61:6012-6019, 2001.*
GenBank Accession No. AC109999.2. *Homo sapiens* chromosome 5 clone CTD-2265M6, complete sequence. Mar. 27, 2002, pp. 1-32.*
Cheon J. et al., Cancer Gene Therapy, 4:359-365 (1997).
Chung Leland W K et al., Urology, 62:44-54 (2003).

* cited by examiner

*Primary Examiner* — Quang Nguyen
(74) *Attorney, Agent, or Firm* — Muncy, Geissler, Olds & Lowe, PLLC

(57) ABSTRACT

An isolated DNA sequence corresponding to a region of the SPARC gene human promoter from base pair −513 to base pair +35 capable of driving the expression of a heterologous gene of interest, that can be associated to any other promoter sequence, such as radiation responsive sequence, hypoxia responsive sequence and free-radical responsive sequence. The invention also provides constructs and DNA recombinant expression viral vectors, comprising the isolated sequence of the SPARC gene human promoter and at least one heterologous gene operably linked thereto, wherein the promoter sequence drives the expression of the at least one heterologous gene in tumor cells. Pharmaceutical compositions and a method for treating tumors are also provided.

13 Claims, 16 Drawing Sheets

SEQUENCE LISTING

```
<160> NUMBER OF SEQ ID NOS: 56

<210> SEQ ID NO 1
<211> LENGTH: 548
<212> TYPE: DNA
<213> ORGANISM: Homo sapiens
<220> FEATURE:
<221> NAME/KEY: misc_feature
<223> OTHER INFORMATION: DNA fragment of the SPARC human promoter.

<400> SEQUENCE: 1
gcagcttgtc ttgtctgtac agtggtaagt cctggccttg cctttgtggc aaatacaacc      60
cccttgaatt gcttggccct tctcagcatt gcctaatatt agggaggact cctgtaaagc     120
tcactggtta gaagatcaag acacttgggc ctggttctgc ccctggggc cattgggtaa     180 ttccttgcag tctccaggcc tcacttgccc tctgaacaag aaagaggctg ttctgggtca     240
tccctccagg cctgtccagc cctggcactc tgtgagtcgg tttaggcagc agccccggaa     300
cagatgaggc aggcagggtt gggacgtttg gtcaggacag cccaccgcaa aaagaggagg     360
aaagaaatga aagacagaga cagctttggc tatgggagaa ggaggaggcc gggggaagga     420
ggagacagga ggaggaggga ccacggggtg gaggggagat agacccagcc cagagctctg     480
agtggtttcc tgttgcctgt ctctaaaccc ctccacattc ccgcggtcct tcagactgcc     540
cggagagc                                                              548

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer
```

```
<400> SEQUENCE: 2
aaccgaagag gaggtggtg                                              19

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
gcaaagaagt ggcaggaaga                                             20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
agaaaatctg gcaccacacc                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
cagaggcgta cagggatagc                                             20

<210> SEQ ID NO 6
<211> LENGTH: 27
<212> TYPE: DNA
<213> ORGANISM: Artificial Sequence
<220> FEATURE:
<223> OTHER INFORMATION: Synthetic Primer

<400> SEQUENCE: 6
ctagctagca gctgggtgtt gtggcat                                     27

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
acgcgtcgac ctcagtggca ggca                                        24

<210> SEQ ID NO 8
<211> LENGTH: 38
<212> TYPE: DNA
<213> ORGANISM: Artificial Sequence
<220> FEATURE:
<223> OTHER INFORMATION: Synthetic Primer

<400> SEQUENCE: 8
cggcctcctc cttctcccct gtctctgtct ttcatttc                         38

<210> SEQ ID NO 9
<211> LENGTH: 26
<212> TYPE: DNA
```

```
<213> ORGANISM: Artificial Sequence
<220> FEATURE:
<223> OTHER INFORMATION: Synthetic Primer

<400> SEQUENCE: 9
ctagctagcg ggagaaggag gaggcc                                    26

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer

<400> SEQUENCE: 10
gcagatctcc tcagtggcag gc                                        22

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
gcacgcgtag ctgggtgttg tgg                                       23

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
cgagatctgc tctccgggca g                                         21

<210> SEQ ID NO 13
<211> LENGTH: 25
<212> TYPE: DNA
<213> ORGANISM: Artificial Sequence
<220> FEATURE:
<223> OTHER INFORMATION: Synthetic Primer

<400> SEQUENCE: 13
cgagatctgg gcagtctgaa ggacc                                     25

<210> SEQ ID NO 14
<211> LENGTH: 23
<212> TYPE: DNA
<213> ORGANISM: Artificial Sequence
<220> FEATURE:
<223> OTHER INFORMATION: Synthetic Primer

<400> SEQUENCE: 14
cgacgcgtgc agcttgtctt gtc                                       23

<210> SEQ ID NO 15
<211> LENGTH: 24
<212> TYPE: DNA
<213> ORGANISM: Artificial Sequence
<220> FEATURE:
<223> OTHER INFORMATION: Synthetic Primer

<400> SEQUENCE: 15
gcagatctag tctgaaggac cgcg                                      24
```

<210> SEQ ID NO 16
<211> LENGTH: 22
<212> TYPE: DNA
<213> ORGANISM: Artificial Sequence
<220> FEATURE:
<223> OTHER INFORMATION: Synthetic Primer

<400> SEQUENCE: 16
gaacgcgtgg gagaaggagg ag                                          22

<210> SEQ ID NO 17
<211> LENGTH: 1246
<212> TYPE: DNA
<213> ORGANISM: Homo sapiens
<220> FEATURE:
<221> NAME/KEY: misc_feature
<223> OTHER INFORMATION: Sequence of the human SPARC promoter
      corresponding to the bases -1175/+71 from the initiation of
      transcription.

<400> SEQUENCE: 17
agctgggtgt tgtggcatgt gcgcctgtaa tcccagctac tctggaggct gaggcgcgat    60
aattgcttga acccgggagg cagaggttgc agtgagccga aatcatacca ctgcactcca   120
gcctgggcga cagagtgagt gagactctgt ctcaaaacaa aacaaaacaa acaaacaaaa   180
aaaccggaaa ccacaaaact ttttgaggac aaggaccagg tatttattaa ttctcatacc   240
tcccagagtg ttaggcacaa ataaacatt caaccaagac ctgttgcact gagcagttca    300
tatataacag gagtgaccca agttgaaacg tagaatcagc cctctcatac cacttttttgc   360 caggtgatca taggcaagtt acttagcatc tatgtttcct tattattaaa atggtcataa   420
ttacaatgcc taagataagg ggttgctgtg aagattatta aatcctcagt aaactttggc   480
tattgttact cctatgatta tcatcaatat catcaattac cttatctgtt caatactggt   540
ggcacaggtc caccagctag atgtctaatc ccttatgtgt ctattagtgg tacaagtgga   600
gtttgagtgg gattttttttt tttaagacca gttccaaatc atcaaggatg ataccactag   660
tagcagcttg tcttgtctgt acagtggtaa gtcctggcct tgcctttgtg gcaaatacaa   720 ccccccttgaa ttgcttggcc cttctcagca ttgcctaata ttagggagga ctcctgtaaa   780
gctcactggt tagaagatca agacacttgg gcctggttct gccccctgggg gccattgggt   840 aattccttgc agtctccagg cctcacttgc cctctgaaca agaaagaggc tgttctgggt   900
catccctcca ggcctgtcca gccctggcac tctgtgagtc ggtttaggca gcagccccgg   960
aacagatgag gcaggcaggg ttgggacgtt tggtcaggac agcccaccgc aaaaagagga  1020
ggaaagaaat gaaagacaga gacagctttg gctatgggag aaggaggagg ccggggggaag  1080 gaggagacag gaggaggagg gaccacgggg tggaggggag atagacccag cccagagctc  1140
tgagtggttt cctgttgcct gtctctaaac ccctccacat tcccgcggtc cttcagactg  1200
cccggagagc gcgctctgcc tgccgcctgc ctgcctgcca ctgagg              1246

<210> SEQ ID NO 18
<211> LENGTH: 1236
<212> TYPE: DNA
<213> ORGANISM: Artificial Sequence
<220> FEATURE:
<223> OTHER INFORMATION: Synthetic modification of the complete SPARC
      promoter -1175/+71, wherein a 10 pb sequence comprised between
      the two GGA boxeshas been deleted.

<400> SEQUENCE: 18
agctgggtgt tgtggcatgt gcgcctgtaa tcccagctac tctggaggct gaggcgcgat    60

| | |
|---|---|
| aattgcttga acccgggagg cagaggttgc agtgagccga aatcatacca ctgcactcca | 120 |
| gcctgggcga cagagtgagt gagactctgt ctcaaaacaa aacaaaacaa acaaacaaaa | 180 |
| aaaccggaaa ccacaaaact ttttgaggac aaggaccagg tatttattaa ttctcatacc | 240 |
| tcccagagtg ttaggcacaa ataaacatt caaccaagac ctgttgcact gagcagttca | 300 |
| tatataacag gagtgaccca agttgaaacg tagaatcagc cctctcatac cacttttgc | 360 |
| caggtgatca taggcaagtt acttagcatc tatgtttcct tattattaaa atggtcataa | 420 |
| ttacaatgcc taagataagg ggttgctgtg aagattatta aatcctcagt aaatgttact | 480 |
| cctatgatta tcatcaatat catcaattac cttatctgtt caatactggt ggcacaggtc | 540 |
| caccagctag atgtctaatc ccttatgtgt ctattagtgg tacaagtgga gtttgagtgg | 600 |
| gatttttttt tttaagacca gttccaaatc atcaaggatg ataccactag tagcagcttg | 660 |
| tcttgtctgt acagtggtaa gtcctggcct tgcctttgtg gcaaatacaa ccccccttgaa | 720 |
| ttgcttggcc cttctcagca ttgcctaata ttagggagga ctcctgtaaa gctcactggt | 780 |
| tagaagatca agacacttgg gcctggttct gcccctgggg gccattgggt aattccttgc | 840 |
| agtctccagg cctcacttgc cctctgaaca agaaagaggc tgttctgggt catccctcca | 900 |
| ggcctgtcca gccctggcac tctgtgagtc ggtttaggca gcagcccgg aacagatgag | 960 |
| gcaggcaggg ttgggacgtt tggtcaggac agcccaccgc aaaaagagga ggaaagaaat | 1020 |
| gaaagacaga gacagctttg gctatgggag aaggaggagg ccggggaag gaggagacag | 1080 |
| gaggaggagg gaccacgggg tggaggggag atagacccag cccagagctc tgagtggttt | 1140 |
| cctgttgcct gtctctaaac ccctccacat tcccgcggtc cttcagactg cccggagagc | 1200 |
| gcgctctgcc tgccgcctgc ctgcctgcca ctgagg | 1236 |

<210> SEQ ID NO 19
<211> LENGTH: 1210
<212> TYPE: DNA
<213> ORGANISM: Homo sapiens

<400> SEQUENCE: 19

| | |
|---|---|
| agctgggtgt tgtggcatgt gcgcctgtaa tcccagctac tctggaggct gaggcgcgat | 60 |
| aattgcttga acccgggagg cagaggttgc agtgagccga aatcatacca ctgcactcca | 120 |
| gcctgggcga cagagtgagt gagactctgt ctcaaaacaa aacaaaacaa acaaacaaaa | 180 |
| aaaccggaaa ccacaaaact ttttgaggac aaggaccagg tatttattaa ttctcatacc | 240 |
| tcccagagtg ttaggcacaa ataaacatt caaccaagac ctgttgcact gagcagttca | 300 |
| tatataacag gagtgaccca agttgaaacg tagaatcagc cctctcatac cacttttgc | 360 |
| caggtgatca taggcaagtt acttagcatc tatgtttcct tattattaaa atggtcataa | 420 |
| ttacaatgcc taagataagg ggttgctgtg aagattatta aatcctcagt aaactttggc | 480 |
| tattgttact cctatgatta tcatcaatat catcaattac cttatctgtt caatactggt | 540 |
| ggcacaggtc caccagctag atgtctaatc ccttatgtgt ctattagtgg tacaagtgga | 600 |
| gtttgagtgg gatttttttt tttaagacca gttccaaatc atcaaggatg ataccactag | 660 |
| tagcagcttg tcttgtctgt acagtggtaa gtcctggcct tgcctttgtg gcaaatacaa | 720 |
| ccccccttgaa ttgcttggcc cttctcagca ttgcctaata ttagggagga ctcctgtaaa | 780 |
| gctcactggt tagaagatca agacacttgg gcctggttct gcccctgggg gccattgggt | 840 |
| aattccttgc agtctccagg cctcacttgc cctctgaaca agaaagaggc tgttctgggt | 900 |
| catccctcca ggcctgtcca gccctggcac tctgtgagtc ggtttaggca gcagcccgg | 960 |

```
aacagatgag gcaggcaggg ttgggacgtt tggtcaggac agcccaccgc aaaaagagga    1020
ggaaagaaat gaaagacaga cagctttg gctatgggag aaggaggagg ccggggaag       1080 gaggagacag gaggaggagg gaccacgggg tggaggggga atagacccag cccagagctc   1140
tgagtggttt cctgttgcct gtctctaaac ccctccacat tcccgcggtc cttcagactg   1200
cccggagagc                                                          1210

<210> SEQ ID NO 20
<211> LENGTH: 1203
<212> TYPE: DNA
<213> ORGANISM: Homo sapiens

<400> SEQUENCE: 20
agctgggtgt tgtggcatgt gcgcctgtaa tcccagctac tctggaggct gaggcgcgat    60
aattgcttga acccgggagg cagaggttgc agtgagccga atcatacca ctgcactcca    120 gcctgggcga cagagtgagt gagactctgt ctcaaaacaa aacaaaacaa acaaacaaaa   180
aaaccggaaa ccacaaaact ttttgaggac aaggaccagg tatttattaa ttctcatacc   240
tcccagagtg ttaggcacaa aataaacatt caaccaagac tgttgcact gagcagttca    300 tatataacag gagtgaccca agttgaaacg tagaatcagc cctctcatac cactttttgc   360
caggtgatca taggcaagtt acttagcatc tatgtttcct tattattaaa atggtcataa   420
ttacaatgcc taagataagg ggttgctgtg aagattatta atcctcagt aaactttggc    480 tattgttact cctatgatta tcatcaatat catcaattac cttatctgtt caatactggt   540
ggcacaggtc caccagctag atgtctaatc ccttatgtgt ctattagtgg tacaagtgga   600
gtttgagtgg gatttttttt tttaagacca gttccaaatc atcaaggatg ataccactag   660
tagcagcttg tcttgtctgt acagtggtaa gtcctggcct tgcctttgtg gcaaatacaa   720
cccccttgaa ttgcttggcc cttctcagca ttgcctaata ttagggagga ctcctgtaaa   780
gctcactggt tagaagatca agacacttgg gcctggttct gccctgggg gccattgggt    840 aattccttgc agtctccagg cctcacttgc cctctgaaca agaaagaggc tgttctgggt   900
catccctcca ggcctgtcca gccctggcac tctgtgagtc ggtttaggca gcagccccgg   960
aacagatgag gcaggcaggg ttgggacgtt tggtcaggac agcccaccgc aaaaagagga  1020
ggaaagaaat gaaagacaga cagctttg gctatgggag aaggaggagg ccggggaag      1080 gaggagacag gaggaggagg gaccacgggg tggaggggga atagacccag cccagagctc  1140
tgagtggttt cctgttgcct gtctctaaac ccctccacat tcccgcggtc cttcagactg  1200
ccc                                                                1203

<210> SEQ ID NO 21
<211> LENGTH: 584
<212> TYPE: DNA
<213> ORGANISM: Homo sapiens

<400> SEQUENCE: 21
gcagcttgtc ttgtctgtac agtggtaagt cctggccttg cctttgtggc aaatacaacc    60
cccttgaatt gcttggccct tctcagcatt gcctaatatt agggaggact cctgtaaagc   120
tcactggtta aagatcaag acacttgggc ctggttctgc ccctggggc cattgggtaa     180 ttccttgcag tctccaggcc tcacttgccc tctgaacaag aaagaggctg ttctgggtca   240
tccctccagg cctgtccagc cctggcactc tgtgagtcgg tttaggcagc agccccggaa   300
cagatgaggc aggcagggtt gggacgtttg gtcaggacag cccaccgcaa aaagaggagg   360
```

```
aaagaaatga aagacagaga cagctttggc tatgggagaa ggaggaggcc gggggaagga    420
ggagacagga ggaggaggga ccacggggtg gaggggagat agacccagcc cagagctctg    480
agtggtttcc tgttgcctgt ctctaaaccc ctccacattc ccgcggtcct tcagactgcc    540
cggagagcgc gctctgcctg ccgcctgcct gcctgccact gagg                     584

<210> SEQ ID NO 22
<211> LENGTH: 541
<212> TYPE: DNA
<213> ORGANISM: Homo sapiens

<400> SEQUENCE: 22
gcagcttgtc ttgtctgtac agtggtaagt cctggccttg cctttgtggc aaatacaacc     60
cccttgaatt gcttggccct ctcagcatt gcctaatatt agggaggact cctgtaaagc    120
tcactggtta aagatcaag acacttgggc ctggttctgc ccctggggc cattgggtaa     180 ttccttgcag tctccaggcc tcacttgccc tctgaacaag aaagaggctg ttctgggtca    240
tccctccagg cctgtccagc cctggcactc tgtgagtcgg tttaggcagc agccccggaa    300
cagatgaggc aggcagggtt gggacgtttg gtcaggacag cccaccgcaa aaagaggagg    360
aaagaaatga aagacagaga cagctttggc tatgggagaa ggaggaggcc gggggaagga    420
ggagacagga ggaggaggga ccacggggtg gaggggagat agacccagcc cagagctctg    480
agtggtttcc tgttgcctgt ctctaaaccc ctccacattc ccgcggtcct tcagactgcc    540
c                                                                    541

<210> SEQ ID NO 23
<211> LENGTH: 537
<212> TYPE: DNA
<213> ORGANISM: Homo sapiens

<400> SEQUENCE: 23
gcagcttgtc ttgtctgtac agtggtaagt cctggccttg cctttgtggc aaatacaacc     60
cccttgaatt gcttggccct ctcagcatt gcctaatatt agggaggact cctgtaaagc    120
tcactggtta aagatcaag acacttgggc ctggttctgc ccctggggc cattgggtaa     180 ttccttgcag tctccaggcc tcacttgccc tctgaacaag aaagaggctg ttctgggtca    240
tccctccagg cctgtccagc cctggcactc tgtgagtcgg tttaggcagc agccccggaa    300
cagatgaggc aggcagggtt gggacgtttg gtcaggacag cccaccgcaa aaagaggagg    360
aaagaaatga aagacagaga cagctttggc tatgggagaa ggaggaggcc gggggaagga    420
ggagacagga ggaggaggga ccacggggtg gaggggagat agacccagcc cagagctctg    480
agtggtttcc tgttgcctgt ctctaaaccc ctccacattc ccgcggtcct tcagact       537

<210> SEQ ID NO 24
<211> LENGTH: 191
<212> TYPE: DNA
<213> ORGANISM: Homo sapiens

<400> SEQUENCE: 24
gggagaagga ggaggccggg ggaaggagga gacaggagga ggaggaccca cggggtggag     60
gggagataga cccagcccag agctctgagt ggtttcctgt tgcctgtctc taaacccctc    120
cacattcccg cggtccttca gactgcccgg agagcgcgct ctgcctgccg cctgcctgcc    180
tgccactgag g                                                         191
```

```
<210> SEQ ID NO 25
<211> LENGTH: 155
<212> TYPE: DNA
<213> ORGANISM: Homo sapiens

<400> SEQUENCE: 25
gggagaagga ggaggccggg ggaaggagga gacaggagga ggagggacca cggggtggag    60
gggagataga cccagcccag agctctgagt ggtttcctgt tgcctgtctc taaaccctc    120 cacattcccg cggtccttca gactgcccgg agagc                              155

<210> SEQ ID NO 26
<211> LENGTH: 148
<212> TYPE: DNA
<213> ORGANISM: Homo sapiens

<400> SEQUENCE: 26
gggagaagga ggaggccggg ggaaggagga gacaggagga ggagggacca cggggtggag    60
gggagataga cccagcccag agctctgagt ggtttcctgt tgcctgtctc taaaccctc    120 cacattcccg cggtccttca gactgccc                                      148

<210> SEQ ID NO 27
<211> LENGTH: 17
<212> TYPE: DNA
<213> ORGANISM: Artificial Sequence
<220> FEATURE:
<223> OTHER INFORMATION: Synthetic Primer

<400> SEQUENCE: 27
tacgactcac tataggg                                                   17

<210> SEQ ID NO 28
<211> LENGTH: 18
<212> TYPE: DNA
<213> ORGANISM: Artificial Sequence
<220> FEATURE:
<223> OTHER INFORMATION: Synthetic Primer

<400> SEQUENCE: 28
atttaggtga cactatag                                                  18

<210> SEQ ID NO 29
<211> LENGTH: 20
<212> TYPE: DNA
<213> ORGANISM: Artificial Sequence
<220> FEATURE:
<223> OTHER INFORMATION: Synthetic Primer

<400> SEQUENCE: 29 attaccctc actaaaggga                                                 20

<210> SEQ ID NO 30
<211> LENGTH: 23
<212> TYPE: DNA
<213> ORGANISM: Artificial Sequence
<220> FEATURE:
<223> OTHER INFORMATION: Synthetic Primer

<400> SEQUENCE: 30
ctttatgttt ttggcgtctt cca                                            23

<210> SEQ ID NO 31
<211> LENGTH: 21
<212> TYPE: DNA
<213> ORGANISM: Artificial Sequence
```

```
<220> FEATURE:
<223> OTHER INFORMATION: Synthetic Primer

<400> SEQUENCE: 31
ctagcaaaat aggctgtccc c                                              21

<210> SEQ ID NO 32
<211> LENGTH: 93
<212> TYPE: DNA
<213> ORGANISM: Artificial Sequence
<220> FEATURE:
<223> OTHER INFORMATION: Synthetic multiple cloning site, included in
      the pADPSY vector

<400> SEQUENCE: 32
ggtaccggag gcctcgctag ccacgcgtgg cggcagatct tgcagatatc cgcggatcga    60
tccgccagta cgtactttcc ttaggcagtc gac                                 93

<210> SEQ ID NO 33
<211> LENGTH: 7303
<212> TYPE: DNA
<213> ORGANISM: Artificial Sequence
<220> FEATURE:
<223> OTHER INFORMATION: Synthetic pAd(I)-Xp shuttle vector

<400> SEQUENCE: 33
ttctcatgtt tgacagctta tcatcatcaa taatatacct tattttggat tgaagccaat    60
atgataatga gggggtggag tttgtgacgt ggcgcggggc gtgggaacgg ggcgggtgac   120
gtagtagtgt ggcggaagtg tgatgttgca agtgtggcgg aacacatgta agcgacggat   180
gtggcaaaag tgacgttttt ggtgtgcgcc ggtgtacaca ggaagtgaca attttcgcgc   240
ggttttaggc ggatgttgta gtaaatttgg gcgtaaccga gtaagatttg gccattttcg   300
cgggaaaact gaataagagg aagtgaaatc tgaataattt tgtgttactc atagcgcgta   360
atatttgtct agggccgcgg ggactttgac cgtttacgtg gagactcgcc caggtgtttt   420
tctcaggtgt tttccgcgtt ccgggtcaaa gttggcgttt tattattata gtcaggggga   480
tcctctagaa ctagtgctag agctcgctga tcagcctcga ctgtgccttc tagttgccag   540
ccatctgttg tttgcccctc ccccgtgcct tccttgaccc tggaaggtgc cactcccact   600
gtcctttcct aataaaatga ggaaattgca tcgcattgtc tgagtaggtg tcattctatt   660
ctggggggtg gggtggggca ggacagcaag ggggaggatt gggaagacaa tagcaggcat   720
gctggggatg gtaccggagg cctcgctagc cacgcgtggc ggcagatctc gggactgaa    780 aatgagacat attatctgcc acggaggtgt tattaccgaa gaaatggccg ccagtctttt   840
ggaccagctg atcgaagagg tactggctga taatcttcca cctcctagcc attttgaacc   900
acctacccct cacgaactgt atgatttaga cgtgacggcc cccgaagatc caacgaggag   960 gcggtttcg cagattttcc ccgactctgt aatgttggcg gtgcaggaag ggattgactt  1020
actcactttt ccgccggcgc ccggttctcc ggagccgcct cacctttccc ggcagcccga  1080
gcagccggag cagagagcct tgggtccggt ttctatgcca aaccttgtac cggaggtgat  1140
cgatcttacc tgccacgagg ctggctttcc acccagtgac gacgaggatg aagagggtga  1200
ggagtttgtg ttagattatg tggagcaccc cgggcacggt tgcaggtctt gtcattatca  1260
ccggaggaat acggggggacc cagatattat gtgttcgctt tgctatatga ggacctgtgg  1320
catgtttgtc tacagtaagt gaaaattatg gcagtgggt gatagagtgg tgggtttggt  1380
gtggtaattt tttttttaat ttttacagtt ttgtggttta agaatttttg tattgtgatt  1440
```

```
tttttaaaag gtcctgtgtc tgaacctgag cctgagcccg agccagaacc ggagcctgca      1500
agacctaccc gccgtcctaa aatggcgcct gctatcctga gacgcccgac atcacctgtg      1560
tctagagaat gcaatagtag tacggatagc tgtgactccg gtccttctaa cacacctcct      1620
gagatacacc cggtggtccc gctgtgcccc attaaaccag ttgccgtgag agttggtggg      1680
cgtcgccagg ctgtggaatg tatcgaggac ttgcttaacg agcctgggca acctttggac      1740
ttgagctgta aacgcccag gccataaggt gtaaacctgt gattgcgtgt gtggttaacg      1800
cctttgtttg ctgaatgagt tgatgtaagt ttaataaagg gtgagataat gtttggatct      1860
tgcagatatc cgcggatcga tccgccagta cgtactttcc ttaggcagtc gacctcgaga      1920
tccagacatg ataagataca ttgatgagtt tggacaaacc acaactagaa tgcagtgaaa      1980
aaaatgcttt atttgtgaaa tttgtgatgc tattgctttta tttgtaacca ttataagctg      2040
caataaacaa gttggggatc tcgaggggg gcccatcgaa ttcctgcagc ccggggggatc      2100
tggaaggtgc tgaggtacga tgagacccg accaggtgca gacctgcga gtgtggcggt      2160
aaacatatta ggaaccagcc tgtgatgctg gatgtgaccg aggagctgag gcccgatcac      2220
ttggtgctgg cctgcacccg cgctgagttt ggctctagcg atgaagatac agattgaggt      2280
actgaaatgt gtgggcgtgg cttaagggtg ggaaagaata tataaggtgg gggtcttatg      2340
tagttttgta tctgttttgc agcagccgcc gccgccatga gcaccaactc gtttgatgga      2400
agcattgtga gctcatattt gacaacgcgc atgcccccat gggccggggt gcgtcagaat      2460
gtgatgggct ccagcattga tggtcgcccc gtcctgcccg caaactctac taccttgacc      2520
tacgagaccg tgtctggaac gccgttggag actgcagcct ccgccgccgc ttcagccgct      2580
gcagccaccg cccgcgggat tgtgactgac tttgctttcc tgagcccgct tgcaagcagt      2640
gcagcttccc gttcatccgc ccgcgatgac aagttgacgg ctcttttggc acaattggat      2700
tctttgaccc gggaacttaa tgtcgttttct cagcagctgt tggatctgcg ccagcaggtt      2760
tctgccctga aggcttcctc ccctcccaat gcggtttaaa acataaataa aaaaccagac      2820
tctgttttgga tttggatcaa gcaagtgtct tgctgtctttt atttaggggt tttgcgcgcg      2880
cggtaggccc gggaccagcg gtctcggtcg ttgagggtcc tgtgtatttt ttccaggacg      2940
tggtaaaggt gactctggat gttcagatac atgggcataa gccgtgtctct ggggtggagg      3000
tagcaccact gcagagcttc atgctgcggg gtggtgtgt agatgatcca gtcgtagcag      3060
gagcgctggg cgtggtgcct aaaaatgtct ttcagtagca agctgattgc caggggcagg      3120
cccttggtgt aagtgtttac aaagcggtta agctgggatg ggtgcatacg tggggatatg      3180
agatgcatct tggactgtat ttttaggttg gctatgttcc cagccatatc cctccgggga      3240
ttcatgttgt gcagaaccac cagcacagtg tatccggtgc acttgggaaa tttgtcatgt      3300
agcttagaag gaaatgcgtg gaagaacttg gagacgccct tgtgacctcc aagattttcc      3360
atgcattcgt cctaatgat ggcaatgggc ccacggggcgg cggcctgggc gaagatattt      3420
ctgggatcac taacgtcata gttgtgttcc aggatgagat cgtcataggc cattttttaca      3480
aagcgcgggc ggagggtgcc agactgcggt ataatggttc catccggccc aggggcgtag      3540
ttaccctcac agatttgcat ttcccacgct ttgagttcag atggggggat catgtctacc      3600
tgcggggcga tgaagaaaac ggtttccggg gtaggggaga tcagctggga agaaagcagg      3660
ttcctgagca gctgcgactt accgcagccg gtgggccgt aaatcacacc tattaccggg      3720
tgcaactggt agttaagaga gctgcagctg ccgtcatccc tgagcagggg ggccacttcg      3780
ttaagcatgt ccctgactcg catgttttcc ctgaccaaat ccgccagaag gcgctcgccg      3840
```

```
cccagcgata gcagttcttg caaggaagca aagtttttca acggtttgag accgtccgcc    3900
gtaggcatgc ttttgagcgt ttgaccaagc agttccaggc ggtcccacag ctcggtcacc    3960
tgctctacgg catctcgatc cagcatatct cctcgtttcg cgggttgggg cggctttcgc    4020
tgtacggcag tagtcggtgc tcgtccagac gggccaggt catgtctttc cacgggcgca     4080
gggtcctcgt cagcgtagtc tgggtcacgg tgaaggggtg cgctccgggc tgcgcgctgg    4140
ccagggtgcg cttgaggctg gtcctgctgg tgctgaagcg ctgccggtct tcgccctgcg    4200
cgtcggccag gtagcatttg accatggtgt catagtccag cccctccgcg gcgtggccct    4260
tggcgcgcag cttgcccttg gaggaggcgc cgcacgaggg gcagtgcaga cttttgaggg    4320
cgtagagctt gggcgcgaga ataccgatt ccggggagta ggcatccgcg ccgcaggccc     4380
cgcagacggt ctcgcattcc acgagccagg tgagctctgg ccgttcgggg tcaaaaacca    4440
ggtttccccc atgcttttg atgcgtttct tacctctggt ttccatgagc cggtgtccac     4500
gctcggtgac gaaaaggctg tccgtgtccc cgtatacaga cttgagaggc ctgtcctcga    4560
gcggtgttcc gcggtcctcc tcgtatagaa actcggacca ctctgagaca aaggctcgcg    4620
tccaggccag cacgaaggag gctaagtggg aggggtagcg gtcgttgtcc actaggggt     4680 ccactcgctc cagggtgtga agacacatgt cgccctcttc ggcatcaagg aaggtgattg    4740
gtttgtaggt gtaggccacg tgaccgggtg ttcctgaagg ggggctataa aaggggggtgg  4800 gggcgcgttc gtcctcactc tcttccgcat cgctgtctgc gagggccagc tgttggggtg   4860
agtactccct ctgaaaagcg ggcatgactt ctgcgctaag attgtcagtt ccaaaaacg     4920 aggaggattt gatattcacc tggcccgcgg tgatgccttt gagggtggcc gcatccatct    4980
ggtcagaaaa gacaatcttt ttgttgtcaa gcttggtggc aaacgacccg tagagggcgt    5040
tggacagcaa cttggcgatg gagcgcaggg ttttggttttt gtcgcgatcg gcgcgctcct  5100
tggccgcgat gtttagctgc acgtattcgc gcgcaacgca ccgccattcg ggaaagacgg    5160
tggtgcgctc gtcgggcacc aggtgcacgc gccaaccgcg gttgtgcagg gtgacaaggt    5220
caacgctggt ggctacctct ccgcgtaggc gctcgttggt ccagcagagg ccggccgacg    5280
cgctgggcta cgtcttgctg gcgttcgcga cgcgaggctg gatggccttc cccattatga    5340
ttcttctcgc ttccggcggc atcgggatgc ccgcgttgca ggccatgctg tccaggcagg    5400
tagatgacga ccatcaggga cagcaaaggc cagcaaaagg ccaggaaccg taaaaaggcc    5460
gcgttgctgg cgttttttcca taggctccgc ccccctgacg agcatcacaa aaatcgacgc   5520
tcaagtcaga ggtggcgaaa cccgacagga ctataaagat accaggcgtt tcccccctgga  5580 agctccctcg tgcgctctcc tgttccgacc ctgccgctta ccggatacct gtccgccttt   5640
ctcccttcgg gaagcgtggc gctttctcat agctcacgct gtaggtatct cagttcggtg   5700
taggtcgttc gctccaagct gggctgtgtg cacgaacccc ccgttcagcc cgaccgctgc   5760
gccttatccg gtaactatcg tcttgagtcc aacccggtaa gacacgactt atcgccactg   5820
gcagcagcca ctggtaacag gattagcaga gcgaggtatg taggcggtgc tacagagttc   5880
ttgaagtggt ggcctaacta cggctacact agaaggacag tatttggtat ctgcgctctg   5940
ctgaagccag ttaccttcgg aaaaagagtt ggtagctctt gatccggcaa acaaaccacc   6000
gctggtagcg gtggtttttt tgtttgcaag cagcagatta cgcgcagaaa aaaaggatct   6060
caagaagatc ctttgatctt ttctacgggg tctgacgctc agtggaacga aaactcacgt   6120
taagggattt tggtcatgag attatcaaaa aggatcttca cctagatcct ttttaaattaa   6180 aaatgaagtt ttaaatcaat ctaaagtata tatgagtaaa cttggtctga cagttaccaa    6240
```

```
tgcttaatca gtgaggcacc tatctcagcg atctgtctat ttcgttcatc catagttgcc   6300
tgactccccg tcgtgtagat aactacgata cgggagggct taccatctgg ccccagtgct   6360
gcaatgatac cgcgagaccc acgctcaccg gctccagatt tatcagcaat aaaccagcca   6420
gccggaaggg ccgagcgcag aagtggtcct gcaactttat ccgcctccat ccagtctatt   6480
aattgttgcc gggaagctag agtaagtagt tcgccagtta atagtttgcg caacgttgtt   6540
gccattgctg caggcatcgt ggtgtcacgc tcgtcgtttg gtatggcttc attcagctcc   6600
ggttcccaac gatcaaggcg agttacatga tcccccatgt tgtgcaaaaa agcggttagc   6660
tccttcggtc ctccgatcgt tgtcagaagt aagttggccg cagtgttatc actcatggtt   6720
atggcagcac tgcataattc tcttactgtc atgccatccg taagatgctt ttctgtgact   6780
ggtgagtact caaccaagtc attctgagaa tagtgtatgc ggcgaccgag ttgctcttgc   6840
ccggcgtcaa cacgggataa taccgcgcca catagcagaa ctttaaaagt gctcatcatt   6900
gggaaaacgt tcttcggggc gaaaactctc aaggatctta ccgctgttga tccagttc    6960 gatgtaaccc actcgtgcac ccaactgatc ttcagcatct tttactttca ccagcgtttc   7020
tgggtgagca aaaacaggaa ggcaaaatgc cgcaaaaaag ggaataaggg cgacacggaa   7080
atgttgaata ctcatactct tcctttttca atattattga agcatttatc agggttattg   7140
tctcatgagc ggatacatat ttgaatgtat ttagaaaaat aaacaaatag gggttccgcg   7200
cacatttccc cgaaaagtgc cacctgacgt ctaagaaacc attattatca tgacattaac   7260
ctataaaaat aggcgtatca cgaggcccct tcgtcttcaa gaa                    7303

<210> SEQ ID NO 34
<211> LENGTH: 28
<212> TYPE: DNA
<213> ORGANISM: Artificial Sequence
<220> FEATURE:
<223> OTHER INFORMATION: Synthetic Primer

<400> SEQUENCE: 34
ccactagtgc tagagctcgc tgatcagc                                        28

<210> SEQ ID NO 35
<211> LENGTH: 24
<212> TYPE: DNA
<213> ORGANISM: Artificial Sequence
<220> FEATURE:
<223> OTHER INFORMATION: Synthetic Primer

<400> SEQUENCE: 35
cggtaccatc cccagcatgc ctgc                                            24

<210> SEQ ID NO 36
<211> LENGTH: 1020
<212> TYPE: DNA
<213> ORGANISM: Artificial Sequence
<220> FEATURE:
<223> OTHER INFORMATION: Synthetic sequence obtained with T3 primer
<220> FEATURE:
<221> NAME/KEY: misc_feature
<222> LOCATION: (1009)..(1009)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t

<400> SEQUENCE: 36
gaatgccctt gatcactatc cggtgaattg aattagcggc cgcgaattcg cccttcgaga    60
```

```
tctccggact gaaaatgaga catattattt gccacggagg tgttattacc gaagaaatgg      120
ccgccagtct tttggaccag ctgatcgaag aggtactggc tgataatctt ccacctccta      180
gccattttga accacctacc cttcacgaac tgtatgattt agacgtgacg gccccgaag       240 atcccaacga ggaggcggtt tcgcagattt ttcccgactc tgtaatgttg gcagtgcagg      300
aagggattga cttactcact tttccgccgg cgcccggttc tccggagccg cctcaccttt      360
cccggcagcc cgagcagccg gagcagagag ccttgggtcc ggtttctatg ccaaaccttg      420
taccggaggt gatcgatctt acctgccacg aggctggctt ccacccagt gacgacgagg       480 atgaagaggg tgaggagttt tgttagatt atgtggagca ccccgggcac ggttgcaggt       540
cttgtcatta tcaccggagg aatacggggg acccagatat tatgtgttcg ctttgctata      600
tgaggacctg tggcatgttt gtctacagta agtgaaaatt atgggcagtg ggtgatagag      660
tggtgggttt ggtgtggtaa ttttttttt aattttttaca gttttgtggt ttaaagaatt      720
ttgtattgtg atttttttaa agggtcctgt gtctgaacct gagcctgagc ccgagccaga      780
accggagcct gcaagaccta cccgccgtcc taaaatggcg cctgctatcc tgagacgccc      840
gacatcacct gtgtctagag aatgcaatag tagtacggat agctgtgact ccggtccttc      900
taacacacct cctgagatac acccggtggt cccgctgtgc ccattaaacc agttgccgtg      960
agagttggtg ggcgtcgcca ggctgtggaa tgtatcgagg acttgcttna cgnccggggc     1020
```

<210> SEQ ID NO 37
<211> LENGTH: 1029
<212> TYPE: DNA
<213> ORGANISM: Artificial Sequence
<220> FEATURE:
<223> OTHER INFORMATION: Synthetic sequence obtained with T7 primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 37

```
ccccattttta tacancatta cgccaagctc anaattaacc ctcactaaag ggactanctc      60
ctgcaggttt aaacnaattc gccccttncgg atccaaacat tatctcaccc tttattaaac     120
ttacatcaac tcattcagca aacaaaggcg ttaaccacac acgcaatcac aggtttacac     180
cttatggcct ggggcgttta cagctcaagt ccaaaggttg cccaggctcg ttaagcaagt      240
cctcgataca ttccacagcc tggcgacgcc caccaactct cacggcaact ggtttaatgg      300
ggcacagcgg gaccaccggg tgtatctcag gaggtgtgtt agaaggaccg gagtcacagc      360
tatccgtact actattgcat tctctagaca caggtgatgt cgggcgtctc aggatagcag      420
gcgccatttt aggacggcgg gtaggtcttg caggctccgg ttctggctcg ggctcaggct      480
caggttcaga cacaggaccc tttaaaaaaa tcacaataca aaattcttta aaccacaaaa      540
```

```
ctgtaaaaat taaaaaaaaa attaccacac caaacccacc actctatcac ccactgccca      600
taattttcac ttactgtaga caaacatgcc acaggtcctc atatagcaaa gcgaacacat      660
aatatctggg tcccccgtat tcctccggtg ataatgacaa gacctgcaac cgtgcccggg      720
gtgctccaca taatctaaca caaactcctc accctcttca tcctcgtcgt cactgggtgg      780
aaagccagcc tcgtggcagg taagatcgat cacctccggt acaaggtttg catagaaac      840 cggacccaag gctctctgct ccggctgctc gggctgccgg gaaaggtgag gcggctccgg      900
agaaccgggc gccggcggaa aagtgagtaa gtcaatccct tcctgcactg ccaacattac      960
agagtcggga aaaatctgcg aaaccgcctc ctcgttggga tcttggggc cgtcacgtct     1020 aatcataca                                                             1029

<210> SEQ ID NO 38
<211> LENGTH: 1562
<212> TYPE: DNA
<213> ORGANISM: Artificial sequence
<220> FEATURE:
<223> OTHER INFORMATION: Synthetic pAd(I)-Xp-E1A

<400> SEQUENCE: 38
tctcaggtgt tttccgcgtt ccgggtcaaa gttggcgttt tattattata gtcaggggga       60
tcctctagaa ctagtgctag agctcgctga tcagcctcga ctgtgccttc tagttgccag      120
ccatctgttg tttgcccctc ccccgtgcct tccttgaccc tggaaggtgc cactcccact      180
gtcctttcct aataaaatga ggaaattgca tcgcattgtc tgagtaggtg tcattctatt      240
ctggggggtg gggtggggca ggacagcaag ggggaggatt gggaagacaa tagcaggcat      300 gctgggatg gtaccggagg cctcgctagc cacgcgtggc ggcagatctc cgggactgaa       360
aatgagacat attatctgcc acggaggtgt tattaccgaa gaaatggccg ccagtctttt      420
ggaccagctg atcgaagagg tactggctga taatcttcca cctcctagcc attttgaacc      480
acctaccctt cacgaactgt atgatttaga cgtgacggcc cccgaagatc caacgagga      540 ggcggtttcg cagattttc ccgactctgt aatgttggcg gtgcaggaag ggattgactt      600
actcactttt ccgccggcgc ccggttctcc ggagccgcct caccttttccc ggcagcccga      660 gcagccggag cagagagcct tgggtccggt ttctatgcca aaccttgtac cggaggtgat      720
cgatcttacc tgccacgagg ctggctttcc acccagtgac gacgaggatg aagagggtga      780
ggagtttgtg ttagattatg tggagcaccc cgggcacggt tgcaggtctt gtcattatca      840
ccggaggaat acggggacc cagatattat gtgttcgctt tgctatatga ggacctgtgg      900
catgtttgtc tacagtaagt gaaaattatg ggcagtgggt gatagagtgg tgggtttggt      960
gtggtaattt ttttttttaat ttttacagtt ttgtggttta agaatttg tattgtgatt      1020 ttttaaaag gtcctgtgtc tgaacctgag cctgagcccg agccagaacc ggagcctgca     1080
agacctaccc gccgtcctaa aatggcgcct gctatcctga cgcccgac atcacctgtg      1140 tctagagaat gcaatagtag tacggatagc tgtgactccg gtccttctaa cacacctcct      1200
gagatacacc cggtggtccc gctgtgcccc attaaaccag ttgccgtgag agttggtggg      1260
cgtcgccagg ctgtggaatg tatcgaggac ttgcttaacg agcctgggca acctttggac      1320
ttgagctgta aacgccccag gccataaggt gtaaacctgt gattgcgtgt gtggttaacg      1380
cctttgtttg ctgaatgagt tgatgtaagt ttaataaagg gtgagataat gtttggatct      1440
tgcagatatc cgcggatcga tccgccagta cgtactttcc ttaggcagtc gacctcgaga      1500
tccagacatg ataagataca ttgatgagtt tggacaaacc acaactagaa tgcagtgaaa      1560
```

-continued aa                                                                  1562

<210> SEQ ID NO 39
<211> LENGTH: 1335
<212> TYPE: DNA
<213> ORGANISM: Artificial Sequence
<220> FEATURE:
<223> OTHER INFORMATION: Synthetic pAd-Xp-E1A

<400> SEQUENCE: 39
tctcaggtgt tttccgcgtt ccgggtcaaa gttggcgttt tattattata gtcagggga      60
tcctctagaa ctagtgtgat caggtaccgg aggcctcgct agccacgcgt ggcggcagat    120
ctccgggact gaaaatgaga catattatct gccacggagg tgttattacc gaagaaatgg    180
ccgccagtct tttggaccag ctgatcgaag aggtactggc tgataatctt ccacctccta    240
gccattttga accacctacc cttcacgaac tgtatgattt agacgtgacg gccccgaag     300
atcccaacga ggaggcggtt tcgcagattt ttcccgactc tgtaatgttg gcggtgcagg    360
aagggattga cttactcact tttccgccgg cgcccggttc tccggagccg cctcaccttt    420
cccggcagcc cgagcagccg gagcagagag ccttgggtcc ggtttctatg ccaaaccttg    480
taccggaggt gatcgatctt acctgccacg aggctggctt tccacccagt gacgacgagg    540
atgaagaggg tgaggagttt gtgttagatt atgtggagca ccccgggcac ggttgcaggt    600
cttgtcatta tcaccggagg aatacggggg acccagatat tatgtgttcg ctttgctata    660
tgaggacctg tggcatgttt gtctacagta agtgaaaatt atgggcagtg ggtgatagag    720
tggtgggttt ggtgtggtaa ttttttttt aattttaca gttttgtggt ttaaagaatt       780
ttgtattgtg atttttttaa aaggtcctgt gtctgaacct gagcctgagc ccgagccaga    840
accggagcct gcaagaccta cccgccgtcc taaaatggcg cctgctatcc tgagacgccc    900
gacatcacct gtgtctagag aatgcaatag tagtacggat agctgtgact ccggtccttc    960
taacacacct cctgagatac acccggtggt cccgctgtgc cccattaaac cagttgccgt   1020
gagagttggt gggcgtcgcc aggctgtgga atgtatcgag gacttgctta acgagcctgg   1080
gcaacctttg gacttgagct gtaaacgccc caggccataa ggtgtaaacc tgtgattgcg   1140
tgtgtggtta acgcctttgt ttgctgaatg agttgatgta agtttaataa agggtgagat   1200
aatgtttgga tcttgcagat atccgcggat cgatccgcca gtacgtactt tccttaggca   1260
gtcgacctcg agatccagac atgataagat acattgatga gtttggacaa accacaacta   1320
gaatgcagtg aaaaa                                                    1335

<210> SEQ ID NO 40
<211> LENGTH: 776
<212> TYPE: DNA
<213> ORGANISM: Artificial sequence
<220> FEATURE:
<223> OTHER INFORMATION: Synthetic sequence obtained with pAd-sense
     primer (pAd(I)F512)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (738)..(739)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t

<400> SEQUENCE: 40
ccctnggact gaagctggcg ttttcaatta tagtcaggng gatcctctag aactagtgct      60
agagctcgct gatcagcctc gactgtgcct tctagttgcc agccatctgt tgtttgcccc    120
tcccccgntg ccttccttga ccctggaagg tgccactccc actgtccttt cctaataaaa    180
tgaggaaatt gcatcgcatt gtctgggtag gtgtcattct attctggggg gtggggtggg    240
gcaggacagc aaggggagg attgggaaga caatagcagg catgctgggg atggtaccgg    300
aggcctcgct agccacgcgt gcagcttgtc ttgtctgtac agtggtaagt cctggccttg    360
cctttgtggc aaatacaacc cccttgaatt gcttggccct tctcagcatt gcctaatatt    420
agggaggact cctgtaaagc tcactggtta gaagatcaag acacttgggc ctggttctgc    480
ccctggggt cattgggtaa ttccttgcag tctccaggcc tcacttgccc tctgaacaag    540
aaagaggctg ttctgggtca tccctccagg cctgtccagc cctggcactc tgtgagtcgg    600
tttaggcagc agccccggaa cagatgaggc aggcagggtt gggacgtttg gtcaggacag    660
cccaccgcaa aaagaggagg aaanaaatga aagacagaga cagctttggc tatgggagaa    720
ngaggangcc gggngaanng atgacacagg angangangg accaccgggt ggaggg        776

<210> SEQ ID NO 41
<211> LENGTH: 507
<212> TYPE: DNA
<213> ORGANISM: Artificial sequence
<220> FEATURE:
<223> OTHER INFORMATION: Synthetic sequence obtained with pAd-sense
      primer (pAd-F512)
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:

-continued

<221> NAME/KEY: misc_feature
<222> LOCATION: (498)..(498)
<223> OTHER INFORMATION: n is a, c, g, or t

<400> SEQUENCE: 41
cncccggntg aagctggcgt ttattnttat agtcaggggg atcctctaga actagtgatc    60
aggtaccgga ggcctcgcta gccacgcgtg cagcttggtc ttggtctgta cagtggtaag   120
tcctggcctt gcctttgtgg caaatacaac ccccttgaat tgcttggccc ttctcagcat   180
tgcctaatat tagggaggac tcctgtaaag ctcactggtt agaagatcaa gacacttggg   240
cctggttctg ccctggggg tcattgggta attccttgca gtctccaggc ctcacttgcc    300
ctctgaacaa gaaagaggct gttctgggtc atccctccag gcctgtccag ccctggcact   360
ctgtgagtcg gtttaggcag cagccccgga acagatgagg caggcaggt tgggacgttt    420 ggtcaggaca gcccaccgca aaagaggag gaaagaaatg aaagacagag acagctttgg    480
ctatgggaga aggaggangg ccgggggg                                       507

<210> SEQ ID NO 42
<211> LENGTH: 22
<212> TYPE: DNA
<213> ORGANISM: Artificial sequence
<220> FEATURE:
<223> OTHER INFORMATION: Synthetic Primer

<400> SEQUENCE: 42 tgttttctc aggtgtttc cg                                               22

<210> SEQ ID NO 43
<211> LENGTH: 23
<212> TYPE: DNA
<213> ORGANISM: Artificial sequence
<220> FEATURE:
<223> OTHER INFORMATION: Synthetic Primer

<400> SEQUENCE: 43
gcccatggct tcgtaccccg gcc                                            23

<210> SEQ ID NO 44
<211> LENGTH: 29
<212> TYPE: DNA
<213> ORGANISM: Artificial sequence
<220> FEATURE:
<223> OTHER INFORMATION: Synthetic Primer

<400> SEQUENCE: 44
gcgtcgactc agttagcctc ccccatctc                                      29

<210> SEQ ID NO 45
<211> LENGTH: 957
<212> TYPE: DNA
<213> ORGANISM: Artificial sequence
<220> FEATURE:
<223> OTHER INFORMATION: Synthetic TK-TOPO-pCR4 plasmid obtained with
      T3 primer

<400> SEQUENCE: 45
gcatctgcgg gggtttcggg gcgaagttac gattcgccct tgcgtcgact cagttagcct    60
cccccatctc ccgggcaaac gtgcgcgcca ggtcgcagat cgtcggtatg agccggggg    120 tggtgacgtg ggtctggacc atcccggagg taagttgcag cagggcgtcc ggcagccgg    180 cgggcgattg gtcgtaatcc aggataaaga cgtgcatggg acggaggcgt ttggccaaga   240
cgtccaaggc ccaggcaaac acgttgtaca ggtcgccgtt ggggccagc aactcggggg    300

```
cccgaaacag ggtaaataac gtgtccccga tatggggtcg tgggcccgcg ttgctctggg    360
gctcggcacc ctggggcggc acggccgtcc ccgaaagctg tccccaatcc tcccgccacg    420
acccgccgcc ctgcagatac cgcaccgtat tggcaagcag cccgtaaacg cggcgaatcg    480
cggccagcat agccaggtca agccgctcgc cggggcgctg gcgtttggcc aggcggtcga    540
tgtgtctgtc ctccggaagg gcccccaaca cgatgtttgt gccgggcaag gtcggcggga    600
tgagggccac gaacgccagc acggcctggg gggtcatgct gcccataagg tatcgcgcgg    660
ccgggtagca caggagggcg gcgatgggat ggcggtcgaa gatgagggtg agggccgggg    720
gcggggcatg tgagctccca gcctcccccc cgatatgagg agccagaacg gcgtcggtca    780
cggcataaag gcatgcccat tgttatctgg gcgcttgtca ttaccaccgc cgcgtccccg    840
ggccgatatc tcaccctggt cgaggcggtg ttgtgtgggg gtagatgttc gcgattggtc    900
tcgcagcccc caagcaactg cagtaaagtc aatcgggcct cggggtaacc gtttagg       957
```

<210> SEQ ID NO 46
<211> LENGTH: 238
<212> TYPE: DNA
<213> ORGANISM: Artificial sequence
<220> FEATURE:
<223> OTHER INFORMATION: Synthetic sequence pAd(I)-F512-TK obtained with
      pAd-sense primer

<400> SEQUENCE: 46

```
ccggctttac gctggcgttt tattattata gtcaggggga tcctctagaa ctagtgctag    60
agctcgctga tcagcctcga ctgtgccttc tagttgccag ccatctgttg tttgcccctc    120
ccccgtgcct tccttgaccc tggaaggtgc cactcccact gtcctttcct aataaaatga    180
ggaaattgca tcgcattgtc tgggtaggtg tcattctatt ctgggggtg gggtgggg       238
```

<210> SEQ ID NO 47
<211> LENGTH: 965
<212> TYPE: DNA
<213> ORGANISM: Artificial sequence
<220> FEATURE:
<223> OTHER INFORMATION: Synthetic sequence pAd(I)-F512-TK obtained
      with pAd-antisense primer

<400> SEQUENCE: 47

```
acggtgttgt taggttctca ttctgttgtg gtttgtccaa actcatcaat gtatcttatc    60
atgtctggat ctcgaggtcg actcagttag cctcccccat ctcccgggca aacgtgcgcg    120
ccaggtcgca gatcgtcggt atggagccgg gggtggtgac gtgggtctgg accatcccgg    180
aggtaagttg cagcagggcg tcccggcagc cggcgggcga ttggtcgtaa tccaggataa    240
agacgtgcat gggacggagg cgtttggcca agacgtccaa ggcccaggca aacacgttgt    300
acaggtcgcc gttgggggcc agcaactcgg ggcccgaaa cagggtaaat aacgtgtccc    360
cgatatgggg tcgtgggccc gcgttgctct ggggctcggc accctggggc ggcacggccg    420
tccccgaaag ctgtccccaa tcctcccgcc acgacccgcc gccctgcaga taccgcaccg    480
tattggcaag cagcccgtaa acgcggcgaa tcgcggccag catagccagg tcaagccgct    540
cgccggggcg ctggcgtttg gccaggcggt cgatgtgtct gtcctccgga agggccccca    600
acacgatgtt tgtgccgggc aaggtcggcg ggatgagggc cacgaacgcc agcacggcct    660 gggggtcat gctgcccata aggtatcgcg cggccgggta gcacaggagg gcggcgatgg    720
gatggcggtc gaagatggag ggtgagggcc ggggggcggg gcatgtgagc tcccagcctc    780
ccccccgata tgaggagcca gaacggcgtc ggtcacggca taaggcatgc ccattgttat    840
```

```
ctgggcgctt gtcattacca ccgcccgcgt ccccggccga tatctcaacc ctgatcgagg    900
cggatgtatg gtggtggtgt agaattgttt cgacgaattt gtctctcgcg aaagaggccc    960
cccca                                                                965
```

<210> SEQ ID NO 48
<211> LENGTH: 25
<212> TYPE: DNA
<213> ORGANISM: Artificial sequence
<220> FEATURE:
<223> OTHER INFORMATION: Synthetic Primer

<400> SEQUENCE: 48

```
cacaaatttc acaaataaag cattt                                          25
```

<210> SEQ ID NO 49
<211> LENGTH: 911
<212> TYPE: DNA
<213> ORGANISM: Artificial sequence
<220> FEATURE:
<223> OTHER INFORMATION: Synthetic sequence (pAd(I)-F512-EGFP) obtained
      with pAd-sense primer, partial sequence of the virus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t

<400> SEQUENCE: 49

```
catcngcnag cggcgctcta tnattatagt catnggatcc tctagaacta gtgctagagc    60
tcgctgatca gcctcgactg tgccttctag ttgccagcca tctgttgttt gcccctcccc    120
cgtgccttcc ttgaccctgg aaggtgccac tcccactgtc ctttcctaat aaaatgagga    180
aattgcatcg cattgtctgg gtaggtgtca ttctattctg gggggtgggg tgggcagga    240 cagcaagggg gaggattggg aagacaatag caggcatgct ggggatggta ccggaggcct    300
cgctagccac gcgtgcagct tgtcttgtct gtacagtggt aagtcctggc cttgcctttg    360
tggcaaatac aaccccttg aattgcttgg cccttctcag cattgcctaa tattagggag    420
gactcctgta aagctcactg gttagaagat caagacactt gggcctggtt ctgccctgg    480 gggtcattgg gtaattcctt gcagtctcca ggcctcactt gccctctgaa caagaaagag    540
gctgttctgg gtcatccctc caggcctgtc cagccctggc actctgtgag tcggtttagg    600
cagcagcccc ggaacagatg aggcaggcag ggttgggacg tttggtcagg acagcccacc    660
gcaaaaagag gaggaaagaa atgaaagaca gagacagctt tggctatggg agaaggagga    720
ggccggggga aggaggagac aggaagagga nggaccacgg ggtggaaggg agatagaccc    780
```

```
agcccagagc tctgagtggt ttccctgttg cctgtctcta aacccctcca cattcccgcg    840
gtccttcaga ctgnccggag agcagatctc cggactgaaa atgagacata ttatttgcca    900
cggaaggtgt t                                                          911
```

<210> SEQ ID NO 50
<211> LENGTH: 908
<212> TYPE: DNA
<213> ORGANISM: Artificial sequence
<220> FEATURE:
<223> OTHER INFORMATION: Synthetic sequence pAd(I)-F512-EGFP obtained
      with pAd-antisense primer, partial sequence of the virus
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 50

```
gcattctagt nctctaangg tccaaactcn ntcaatgtat cttatcatgt ctggatctcg     60
aggtcgacca ctgtgctggc ggccgcttta cttgtacagc ctcgtccatg ccagagtga    120 tcccggcggc ggtcacgaac tccagcagga ccatgtggat cgcgcttctc gttggggtct   180
ttgctcaggg cggactgggt gctcaggtag tggttgtcgg gcagcagcac ggggccgtcg   240
ccgatggggg tgttctgctg gtagtggtcg gcgagctgca cgctgccgtc ctcgatgttg   300
tggcggatct tgaagttcac cttgatgccg ttcttctgct tgtcggccat gatatagacg   360
ttgtggctgt tgtagttgta ctccagcttg tgccccagga tgttgccgtc ctccttgaag   420
tcgatgccct tcagctcgat gcggttcacc agggtgtcgc cctcgaactt cacctcggcg   480
cgggtcttgt agttgccgtc gtccttgaag aagatggtgc gctcctggac gtagccttcg   540
ggcatggcgg acttgaagaa gtcgtgctgc ttcatgtggt cggggtagcg gctgaagcac   600
tgcacgccgt aggtcagggt ggtcacgagg gtgggccagg gcacgggcag cttgccggtg   660
gtgcagatga acttcagggt cagcttgccg taagtggcat cgccctcgcc ctcgccggac   720
acgctgaact tgtggccgtt tacgtcgccg tccagctcga ccaggatggg caccaccccg   780
gtgaacagct cctcgccctt gctcaccatg gttgtggcca tattatcatc gtgtttttca   840
aaggaaaacc acgtccccgt ggttcggggg gcctaagacg ttttttttaac ctcgactaaa   900 acacatgt                                                             908
```

<210> SEQ ID NO 51
<211> LENGTH: 842
<212> TYPE: DNA
<213> ORGANISM: Artificial sequence
<220> FEATURE:
<223> OTHER INFORMATION: Modified adenovirus Ad-F512; sequence obtained
      with pAd-sense primer, partial sequence of the virus
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (19)..(19)

```
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t

<400> SEQUENCE: 51
tccnngtaat cagnnagcng ctannaaggg tttgtcnnna gggatcctct agaactagtg      60
ntcaggtacc ggaggcctcg ctagccacgc gtgcagcttg tcttgtctgt acagtggtaa    120
gtcctggcct tgcctttgtg gcaaatacaa ccccttgna attgcttggc ccttctcagc     180
attgcctaat attagggagg actcctgtaa agctcactgg ttagaagatc aaggacactt    240
gggcctggtt ctgcccctgg gggtcattgg gtaattcctt gcagtctcca ggcctcactt    300
gccctctgaa caagaaagag gctgttctgg gtcatccctc caggcctgtc agccctggc    360
actctgtgga gtcggtttag gcagcagccc cgggaacaga tgaggcaggc agggttggga    420
cgtttggtca ggacagccca ccgcaaaaag aggaggaaag aaatgaaaga cagagacagc    480
tttggctatg ggagaaggag gaggccgggg gaaggaggag acaggaggag gagggaccac    540
ggggtggagg ggagatagac ccagcccaga gctctgagtg gtttcctgtt gcctgtctct    600
aaacccctcc acattcccgc ggtccttcag actgcccgga gagcagatct ccggactgaa    660
aatgagacat attatttgcc acggaggtgt tattaccgaa gaaatggccg ccagtctttt    720
ggaccagctg atcgaagagg tactggctga taatcttcca cctcctagcc attttgaacc    780
acctaccctt cacgnaactg tatgatttag acgtgacggg cccccgaaga tcccaacgag    840
ga                                                                    842

<210> SEQ ID NO 52
<211> LENGTH: 851
<212> TYPE: DNA
<213> ORGANISM: Artificial sequence
<220> FEATURE:
<223> OTHER INFORMATION: Modified adenovirus Ad-F512; sequence obtained
      with pAd-antisense primer, partial sequence of the virus
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
```

```
<222> LOCATION: (19)..(19)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t

<400> SEQUENCE: 52
aaaangacgn cngnaagcnc taaggggcna attncaaagg gnatcttatc atgtctggat      60
ctcgnaggct cggactgcct aaggtaaagn acgtactggc ggnatcgaat ccgcgggata    120
tctgctaagn atccaaacat tatctcaccc tttattaaac ttacatcaac tcattcagca    180
aacaaaggcg ttaaccacac acgcaatcac aggctttaca ccttatggcc tggggcgttt    240
acagctcaag tccaaaggtt gcccaggctc gttaagcaag tcctcgatac attccacagc    300
ctggcgacgc ccaccaactc tcacggcaac tggtttaatg gggcacagcg ggaccaccgg    360
gtgtatctca ggaggtgtgt tagaaggacc ggnagtcaca gctatccgta ctactattgc    420
attctctaga cacaggtgat gtcgggcgtc tcaggatagc aggcgccatt ttaggacggc    480
gggtaggtct tgcaggctcc ggttctggct cgggctcagg ctcaggttca gacacaggna    540
ccctttaaaa aaatcacaat acaaaattct ttaaaccaca aaactgtaaa aattaaaaaa    600
aaaattacca caccaaaccc accactctat cacccactgc ccataatttt cacttactgt    660
agacaaacat gccacaggtc ctcatatagc aaagcgaaca cataatatct gggtcccccg    720
tattcctccg ggtgataatg gacaagacct gcaaccgtgg cccggggtgc tccacataaa    780
tctaacacaa actcctcacc ctcttcatcc tcgtcgtcac tgggtggaaa gccagccctc    840
gtggcaggta a                                                        851

<210> SEQ ID NO 53
<211> LENGTH: 854
<212> TYPE: DNA
<213> ORGANISM: Artificial sequence
<220> FEATURE:
<223> OTHER INFORMATION: Modified adenovirus Ad(I)-F512-TK; sequence
      obtained with pAd-sense primer, partial sequence of the virus
```

<400> SEQUENCE: 53

```
aaaaagaacc ttttaatgcg cgctcggtcg cgttttatta ttatagtcag ggggatcctc    60
tagaactagt gctagagctc gctgatcagc ctcgactgtg ccttctagtt gccagccatc   120
tgttgtttgc ccctcccccg tgccttcctt gaccctggaa ggtgccactc ccactgtcct   180
ttcctaataa aatgaggaaa ttgcatcgca ttgtctgggt aggtgtcatt ctattctggg   240
gggtggggtg gggcaggaca gcaaggggga ggattgggaa gacaatagca ggcatgctgg   300
ggatggtacc ggaggcctcg ctagccacgc gtgcagcttg tcttgtctgt acagtggtaa   360
gtcctggcct tgcctttgtg gcaaatacaa ccccccttgaa ttgcttggcc cttctcagca   420
ttgcctaata ttagggagga ctcctgtaaa gctcactggt tagaagatca agacacttgg   480
gcctggttct gccccctgggg gtcattgggt aattccttgc agtctccagg cctcacttgc   540
cctctgaaca gaaagaggc tgttctgggt catccctcca ggcctgtcca gccctggcac   600
tctgtgagtc ggtttaggca gcagcccgg aacagatgag gcaggcaggg ttgggacgtt   660
tggtcaggac agcccaccgc aaaaagagga ggaaagaaat gaaagacaga gacagctttg   720
gctatgggag aaggaggagg ccgggggaaa ggaggagaca ggaggaggag ggaccacggg   780
gtggagggg agatagaccc agccagagct cctgagtgtt tcctgttggc ctgtctctaa   840
accccccctcc caca                                                   854
```

<210> SEQ ID NO 54
<211> LENGTH: 840
<212> TYPE: DNA
<213> ORGANISM: Artificial sequence
<220> FEATURE:
<223> OTHER INFORMATION: Modified adenovirus Ad(I)-F512-TK; sequence
      obtained with pAd-antisense primer, partial sequence of the virus

<400> SEQUENCE: 54

```
ttcccatttt taaccttatg tccttgattg ttgattcact ctcatgttct atctgtctgg    60
tctcgaggcg cttaaaaaac tcccccatct cccgggcaaa cgtgcgcgcc cctgccgcaa   120
atcgtcggta tggagccggg ggtggtgacg tgggtctgga ccatcccgga ggtaagttgc   180
agcagggcgt cccggcagcc ggcgggcgat tggtcgtaat ccaggataaa gacgtgcatg   240
gacggaggc gtttggccaa gacgtccaag gcccaggcaa acacgttgta caggtcgccg   300
ttgggggcca gcaactcggg ggcccgaaac agggtaaata acgtgtcccc gatatggggt   360
cgtgggcccg cgttgctctg gggctcggca ccctggggcg gcacggccgt ccccgaaagc   420
tgtccccaat cctcccgcca cgacccgccg ccctgcagat accgcaccgt attggcaagc   480
agcccgtaaa cgcggcgaat cgcggccagc atagccaggt caagccgctc gccggggcgc   540
tggcgtttgg ccaggcggtc gatgtgtctg tcctccggaa gggcccccaa cacgatgttt   600
gtgccgggca aggtcggcgg gatgagggcc acgaacgcca gcacggcctg gggggtcatg   660
ctgcccataa ggtatcgcgc ggccggggta gcacaggagg gcggcgatgg ggatggcggt   720
cgaagatgag ggtgagggcc gggggcggg gcatgtgagc tcccagcctc cccccgatt    780
tgaggagcca gaacggcgtc gggtcacggc taaggcatgc ccattggtaa tcggggccct   840
```

<210> SEQ ID NO 55
<211> LENGTH: 833
<212> TYPE: DNA
<213> ORGANISM: Artificial sequence
<220> FEATURE:
<223> OTHER INFORMATION: Modified adenovirus Ad(I)-F512(E3); sequence
      obtained with pAd-sense primer, partial sequence of the virus

```
<400> SEQUENCE: 55
cctggcatct ttttgaaagt cggatcttgt cgcgtttatt attatagtca gggggatcct    60
ctagaactag tgctagagct cgctgatcag cctcgactgt gccttctagt tgccagccat   120
ctgttgtttg cccctccccc gtgccttcct tgaccctgga aggtgccact cccactgtcc   180
tttcctaata aaatgaggaa attgcatcgc attgtctggg taggtgtcat tctattctgg   240
ggggtggggt ggggcaggac agcaaggggg aggattggga agacaatagc aggcatgctg   300
gggatggtac cggaggcctc gctagccacg cgtgcagctt gtcttgtctg tacagtggta   360
agtcctggcc ttgcctttgt ggcaaataca accccttga attgcttggc ccttctcagc    420
attgcctaat attagggagg actcctgtaa agctcactgg ttagaagatc aagacacttg   480
ggcctggttc tgcccctggg ggtcattggg taattccttg cagtctccag gcctcacttg   540
ccctctgaac aagaaagagg ctgttctggg tcatccctcc aggcctgtcc agccctggca   600
ctctgtgagt cggtttaggc agcagccccg aacagatga ggcaggcagg gttgggacgt    660
ttggtcagga cagcccaccg caaaaagagg aggaaagaaa tgaaagacag agacagcttt   720
ggctatggga gaaggaggag gccggggaa ggaggagaca ggaggaggag ggaccacggg    780
gtggagggga gatagaccca gcccagagct ctgagtggtt tcctgtttgc ctg          833

<210> SEQ ID NO 56
<211> LENGTH: 816
<212> TYPE: DNA
<213> ORGANISM: Artificial sequence
<220> FEATURE:
<223> OTHER INFORMATION: Modified adenovirus Ad(I)-F512(E3); sequence
      obtained with pAd-antisense primer, partial sequence of the virus

<400> SEQUENCE: 56
cctcatcccc taacgcatcc gcctctgaat gtgatgtcca actcatcatg tatcttatca    60
tgtctggatc tcgcggtctc cccctgtgct ggcggccgct ttacttgtac agctcgtcca   120
tgtttgagag tgatcccggc ggcggtcacg aactccagca ggaccatgtg atcgcgcttc   180
tcgttggggt ctttgctcag gcggactgg gtgctcaggt agtggttgtc gggcagcagc    240
acggggccgt cgccgatggg ggtgttctgc tggtagtggt cggcgagctg cacgctgccg   300
tcctcgatgt tgtggcggat cttgaagttc accttgatgc cgttcttctg cttgtcggcc   360
atgatataga cgttgtggct gttgtagttg tactccagct tgtgcccag gatgttgccg    420
tcctccttga agtcgatgcc cttcagctcg atgcggttca ccagggtgtc gccctcgaac   480
ttcacctcgg cgcgggtctt gtagttgccg tcgtccttga agaagatggt gcgctcctgg   540
acgtagcctt cgggcatggc ggacttgaag aagtcgtgct gcttcatgtg gtcggggtag   600
cggctgaagc actgcacgcc gtaggtcagg gtggtcacga gggtgggcca gggcacgggc    660
agcttgccgg tggtgcagat gaacttcagg gtcagcttgc cgtaggtggc atcgccctcg   720
ccctcgccgg acacgctgaa cttgtggccg tttacgtcgc cgtccagctc gacagggatg   780
ggcaccaccc cggtgaacag ctcctcgccc ttgctc                              816
```

ISOLATED DNA FRAGMENT OF THE SPARC HUMAN PROMOTER AND ITS USE FOR DRIVING THE EXPRESSION OF AN HETEROLOGOUS GENE IN TUMOR CELLS

CROSS-REFERENCE TO RELATED APPLICATIONS

This application is a U.S. National Stage Application of International Application No. PCT/US2007/010196, filed on Apr. 28, 2007, which claims the benefit of Argentina Patent Application No. P20060101724, filed on Apr. 28, 2006. The contents of each of these prior applications are incorporated herein by reference in their entireties.

FIELD OF THE INVENTION

The present invention refers to the field of gene therapy. In particular, the present invention refers to an isolated DNA sequence having promoter activity, capable of driving the expression of a gene of interest, particularly in a tumor cell. More particularly, the present invention refers to vectors containing a DNA fragment isolated from the SPARC promoter associated to a gene of interest, to pharmaceutical compositions and its use in cancer therapy.

BACKGROUND OF THE INVENTION

The SPARC protein (secreted protein, acidic and cystein-rich protein) also known as osteonectin or BM40, is a secreted glycoprotein, highly distributed in human and non-human tissue, which functions and effects are wide and various. It has been found that it interacts with extracellular matrix components, with growth factors, with cytokines and with the expression of matrix metalloproteinases.

The SPARC protein has been initially described by Ledda M. F. et. al. (Ledda, M. F., Adris, S., Bravo, A. I., Kairiyama, C., Bover, L., Chernajovsky, Y., Mordoh, J., and Podhajcer, O. L., *Suppression of SPARC expression by antisense RNA abrogates the tumorigenicity of human melanoma cells*. Nat Med, 3: 171-176, 1997) as having a central role in the malignity of human melanoma. Subsequent studies showed that SPARC over-expression is associated to the malignant progression of various tumor types (Porte, H., Triboulet, J. P., Kotelevets, L., Carrat, F., Prevot, S., Nordlinger, B., DiGioia, Y., Wurtz, A., Comoglio, P., Gespach, C., and Chastre, E. *Overexpression of stromelysin-3, BM-40/SPARC, and MET genes in human esophageal carcinoma: implications for prognosis*. Clin Cancer Res, 4: 1375-1382, 1998). The SPARC protein is highly expressed both in endothelium and activated fibroblasts of in vivo tumors (Lane, T. F. and Sage, E. H. *The biology of SPARC, a protein that modulates cell-matrix interactions*. Faseb J, 8: 163-173, 1994).

Human SPARC promoters (Hafner, M., Zimmermann, K., Pottgiesser, J., Krieg, T., and Nischt, R. *A purine-rich sequence in the human BM-40 gene promoter region is a prerequisite for maximum transcription*. Matrix Biol, 14: 733-741, 1995), murine SPARC promoters (McVey, J. H., Nomura, S., Kelly, P., Mason, I. J., and Hogan, B. L. *Characterization of the mouse SPARC/osteonectin gene. Intron/exon organization and an unusual promoter region*. J Biol Chem, 263: 11111-11116, 1988) and bovine SPARC promoters (Young, M. F., Findlay, D. M., Dominguez, P., Burbelo, P. D., McQuillan, C., Kopp, J. B., Robey, P. G., and Termine, J. D. *Osteonectin promoter. DNA sequence analysis and S1 endonuclease site potentially associated with transcriptional control in bone cells*. J Biol Chem, 264: 450-456, 1989) have been cloned and characterized. The comparison between these promoters shows that, similarly to what it is observed at gene level, a high sequence homology occurs.

The structure of the human SPARC promoter is shown in FIG. 1, wherein the first exon, the GGA1 and GGA2 boxes, the 10 nucleotide Inter-CGA region separating them and the TATA non-consensus sequence are depicted. The human SPARC promoter lacks a TATA consensus box (Breathnach, R. et al., *Organization and expression of eucaryotic split genes coding for proteins*, Annu Rev Biochem, 50: 349-383, 1981) but contains a so-called TATA-like element that shares some bases with the conventional sequence. The promoter has two GCA1 and GCA2 boxes, of which the GCA1 box exhibits a great similarity between the human and bovine species.

Hafner et al. observed that the GCA1 box is necessary and sufficient for obtaining a maximum transcriptional activity, while the spacing element separating the two CGA boxes has a negative effect on its expression (Hafner M. et al., 1995). It is important to note that this group has demonstrated that, in humans, the promoter region containing only the CGA boxes is not sufficient by itself to confer expression specificity in different cell lines. Dominguez et. al. described the region between bases −504 to +11 of the bovine promoter as a positive element for SPARC transcription in fetal bovine cells. This fragment also confers specific expression, showing higher activity in cells with a higher expression level of SPARC mRNA (Dominguez, P., Ibaraki, K., Robey, P. G., Hefferan, T. E., Termine, J. D., and Young, M. F. *Expression of the osteonectin gene potentially controlled by multiple cis-and trans-acting factors in cultured bone cells*. J Bone Miner Res, 6: 1127-1136, 1991). They also observed that only the GC box (which is a common element in many promoter regions and their consensus sequence is GGGCGG, may be present in more than one copy. It is located between the −40 to −100 bp) and the GCA1 box are not sufficient for the maximum SPARC expression in bovine bone cells, and that the region located between the bases −927 to −504 produces a dramatic inhibition of transcription.

The gene therapy potentially represents one of the most important developments taking place in medicine. In order to modify a specific cell or tissue type, therapeutic genes have to be efficiently administered to the cell so that the gene expresses in the appropriate level and for a sufficient amount of time. Two types of strategy are being applied for DNA supply to cells, these are by viral and non-viral vectors. Even though a great number of virus destined to gene transfer have been developed, the major interest has been centered in retrovirus, adenovirus, adeno-associated virus and herpes simplex virus type 1. The first generation adenovirus are defective in E1A protein, hence they do not replicate. The early E1A protein is the first protein that produces the viral DNA inside the cell. E1A has many functions such as helping other viral proteins to be produced and stimulating the cell growth by bonding Rb and releasing E2F, facilitating viral transcription and replication. Even though those E1A protein defective adenovirus were successfully used as vectors in cancer pre-clinical models, the same results were not achieved when used in clinical trials, being its low in vivo transduction capacity one of the major problems (Vile, R. *Cancer gene therapy—new approaches to tumour cell killing*. J Gene Med, 2: 141-143, 2000).

One way to overcome this drawback has been the creation of a new generation of vectors capable of conditionally replicating in the tumor environment; these vectors are called CRAd (Conditionally Replicative Adenovirus or Oncolytic adenovirus). CRAds are constructed by modifying the adenoviral genome in order to regulate the expression of E1A protein with a promoter that is specifically active in the required tissue or cell type, in such a way to prevent damage to surrounding tissues.

In the last years, several research groups have devoted to the recombinant adenovirus construction. This way, some of the viral genes that had been removed in the past are being re-inserted again given that they enhance viral replication. That is the case of the E3 region. E3 is a viral DNA fragment encoding 9 proteins, the main function of which is the inhibition of cell death induced by the host immune response. Among the 9 proteins, ADP (Adenoviral Death Protein) stands out, has a contradictory function when compared to their E3 mates, because it promotes the late cell lysis in the viral infection cycle to allow for the release of mature virions to the cell microenvironment. Cells infected with an non-expressing ADP adenovirus have been shown to remain viable for a longer time than cells infected with the wild type adenovirus (Tollefson, A. E. et al. *The E3-11.6-kDa adenovirus death protein (ADP) is required for efficient cell death: characterization of cells infected with adp mutants*, Virology, 220: 152-162, 1996; Tollefson, A. E et al., *The adenovirus death protein (E3-11.6K) is required at very late stages of infection for efficient cell lysis and release of adenovirus from infected cells*, J Virol, 70. 2296-2306, 1996; Kruyt, F. A. et al., *A new generation of conditionally replicating adenoviruses: pairing tumor selectivity with maximal oncolysis*, Hum Gene Ther, 13: 485-495, 2002. ).

One of the most attractive ways of gene therapy is the use of suicide genes. The basis of the system consists of introducing a gene encoding an enzyme with the capacity of metabolizing a non-toxic prodrug turning it into a toxic drug. One of the mostly used genes is the Herpes simplex virus thymidine kinase or HSV/TK, which codifies for an enzyme capable of phosphorilating the prodrug acyclovir/ganciclovir (commonly used antiviral for viral infections), a guanosine analogue. In its phosphorilated form, the anti-herpetic agent is incorporated to the DNA molecule, avoiding its duplication and causing cell death (Moolten, F. L., *Drug sensitivity ("suicide") genes for selective cancer chemotherapy*, Cancer Gene Ther, 1: 279-287, 1994). The neighbor non-transduced tumor cells may also be eliminated by the so-called bystander effect, which allows the toxic metabolites to be transferred from an affected cell to a non-affected cell.

A tumor is formed by tumor cells, fibroblasts and endothelial cells. This is why an effective therapy with viral vectors requires the virus to be able to replicate in these three cell types, which are responsible of tumor progression. Given that SPARC is over-expressed in all these cell types, it represents a good candidate for the construction of a CRAd, such that the SPARC promoter drives the gene of interest, such as an E1A gene and eventually another therapeutic gene. In this sense, the tumor cells would be eliminated by the replication of the virus itself or by the action of the toxic drug produced in the tumor environment.

BRIEF DESCRIPTION OF THE INVENTION

It is therefore an object of the present invention to provide an isolated DNA sequence, with promoter activity, capable of driving the expression of a gene of interest, particularly in a tumor cell.

The present invention provides an isolated fragment, from the human SPARC gene promoter, capable of driving the expression of a gene of interest, particularly in a tumor cell.

More particularly, the invention provides an isolated DNA sequence-comprising the polynucleotide sequence SEQ ID NO 1 that corresponds to a region of the human SPARC promoter from base pair −513 to base pair +35 or a fragment or variant of said polynucleotide sequence that has been modified by insertion, substitution or deletion of one or more nucleotides, and which has a substantially equivalent function.

According to an additional aspect, it is provided an isolated DNA recombinant expression construct that comprises the promoter sequence of the invention operably linked to a gene of interest.

According to another additional aspect, the polynucleotide sequence SEQ ID NO 1, that corresponds to a region of the human promoter of the SPARC gene according to the present invention may also be associated to any other promoter/regulating sequence, such as sequences responsive to radiation, hypoxia, free-radicals, etc.

According to yet another relevant aspect of the present invention, it is provided a viral recombinant expression vector, containing the previously defined DNA promoter sequence of the invention and/or the previously defined construct of the invention, wherein the DNA promoter sequence is operably linked to a therapeutic gene of interest.

The invention also provides a method for expressing foreign DNA in a host cell that comprises introducing in the host cell a DNA recombinant expression construct or a viral recombinant expression vector of the invention comprising the promoter DNA molecule of polynucleotide sequence SEQ ID NO 1 operably linked to a foreign DNA encoding a desired polypeptide or RNA, wherein said foreign DNA is expressed.

The invention also provides a method for treating a tumor in a patient suffering therefrom, that comprises administering to the patient an effective amount of a pharmaceutical composition comprising a DNA recombinant expression construct or a viral recombinant expression vector, comprising the promoter sequence of the invention, capable of driving the viral replication and/or the expression of a therapeutic gene of interest, operably linked thereto.

BRIEF DESCRIPTION OF THE DRAWINGS

FIG. 3 shows two schemes of the SPARC promoter region where the different fragments derive from.

FIG. 10A shows the tumor growth curve for the assay with Ad(I)F512-TK. FIG. 10B shows the tumor growth curve of the animals in the first assay with Ad-F512. FIG. 10C shows tumors treated with Ad-β-gal and with Ad-F512. FIG. 10D shows histological photographs of the regions shown in 10C, 14 days after. FIG. 10E shows Kaplan-Meier curve for assay B. FIG. 10F shows Kaplan-Meier curve for the second assay with Ad-F512.

FIG. 12A shows CRAds photographs taken after 10 days post-infection in normal melanocytes; photographs of AD-wt and no-treatment (PBS) controls are included; FIG. 12B shows the cytopathic effect on normal CCD841 colon cells; FIG. 12C shows the cytopathic effect on normal MCF12A breast cells; FIG. 12D shows the lytic effect on microendothelial cells; FIG. 12E shows the viral effect on keratinocytes and fibroblasts (CCD1140 and Malme-3).

FIG. 13A shows the assay with SB2 melanoma cells; FIG. 13B shows the survival of hMEC-1 cells in the presence of GCV and GCV+virus; FIG. 13C shows the cytopathic effect on BAEC cells.

FIG. 14A shows assays with SB2/WI-38/hMEC-1 tumors treated with Ad-F512; FIG. 14B shows assays with SB2/WI-38 tumors treated with Ad-F512; FIG. 14C shows SB2/hMEC-1 tumors treated with Ad-F512; FIG. 14D shows SB2/WI-38 tumors treated with Ad(I)-FS12-TK+GCV, n=5 or PBS+GCV n=4, where n is the number of treated animals.

FIG. 15A shows assays on LoVo tumors treated with Ad-F512 (n=7), Ad(I)-F512-TK (n=6) or PBS (n=7); FIG. 15B shows the average of LoVo/hMEC-1 tumors treated with Ad-F512 (n=6), Ad(I)-F512-TK+GCV (n=6) or PBS +GCV (n=6); FIG. 15C shows the tumor growth of Mia-PaCa/hMEC-1 treated with Ad-F512 (n=6), Ad(I)-F512-TK+GCV (n=6), or PBS+GCV (n=5). In all cases n indicates the number of treated animals.

DETAILED DESCRIPTION OF THE INVENTION

Figure 1:
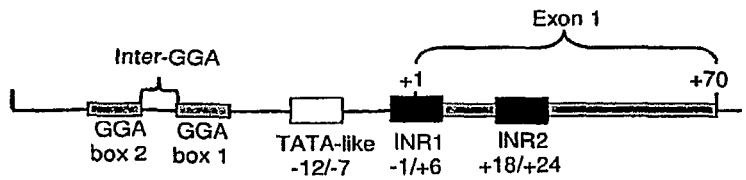
FIG. 1 shows a structure scheme of the human SPARC promoter, HSBM40DNA (Genbank #X88259)

As disclosed above, the present invention provides in a main aspect, a DNA isolated sequence comprising the polynucleotide sequence SEQ ID NO 1, which corresponds to a region of the human SPARC gene promoter from base pair −513 to base pair +35 or a fragment or variant of said polynucleotide sequence, which has been modified by insertion, substitution or deletion of one or more nucleotides, and which has a substantially equivalent function.

The term "isolated" as used herein, means substantially separated or purified with respect to contaminant sequences in the cell or organism in which the nucleic acid is naturally present and includes nucleic acids purified by standard purification techniques as well as nucleic acids prepared either by recombinant technique or chemical synthesis.

The term "variant" as used herein, refers to a DNA molecule wherein the nucleotide sequence is substantially identical to the sequence established as SEQ ID NO 1. The variant may be achieved by means of modifications such as insertion, substitution or deletion of one or more nucleotides, provided that those modifications are neutral mutations and they do not affect the performance of the DNA molecule.

A "fragment" of nucleic acid sequence according to the present invention is a nucleic acid sequence portion that is shorter in length than the complete sequence and comprises at least a minimum length capable of getting specifically hybridized with the nucleic acid sequence of the present invention under astringent conditions, said fragment keeping the biological conditions required in the present invention.

The present invention also provides a recombinant expression construct effective in driving transcription of a selected codifying sequence that comprises: (a) a DNA sequence corresponding to the human SPARC promoter; and (b) a sequence codifying for a gene of interest, operably linked to the promoter in (a) in such a way that the sequence of the gene of interest may be transcribed and translated in a host cell.

According to one embodiment, the preferred DNA sequence corresponding to the human SPARC promoter goes from base pair −513 base pair to +35 according to sequence shown in SEQ ID NO 1 of the Sequence Listing.

A "heterologous" gene as used herein, means a DNA sequence encoding an amino acid or protein sequence of interest, in association with another DNA sequence, such that said association is not present in nature.

In general, "a therapeutic gene" as used herein, means a DNA sequence encoding an amino acid or protein sequence, capable of eliciting a therapeutic effect on the host cells. Preferably, according to one embodiment of the present invention the host cells are tumor cells, more particularly, the tumor cells are melanoma cells, breast cells, colon cells, cervix cells.

According to a preferred embodiment, the gene of interest may be selected from: the E1A gene, a suicide gene such as the hsv-TK gene, the adenoviral genomic region called E3, the gene of an interleukin such as IL-10, IL-12 or IL-23, etc.

According to particular embodiments, the polynucleotide sequence SEQ ID NO 1 that corresponds to a region of the human SPARC gene promoter, according to the present invention, may drive genes by itself or may be associated with sequences responsive to radiation, hypoxia, free-radicals, etc. These are defined DNA sequences, which are usually located upstream of said promoter. One characteristic example of this kind of combinations is the use therein of the hypoxia responsive element (HRE) which has already been used for potentiating the transcriptional activity of a promoter or responsive element under low oxygen pressure conditions. Hernandez-Alcoceba et. al. have used the hypoxia responsive elements (HRE) for potentiating the promoter response containing estrogen responsive elements (ERE) in breast tumors (Hernandez-Alcoceba R, Pihalja M, Nunez G, Clarke M F, *Evaluation of a new dual-specificity promoter for selective induction of apoptosis in breast cancer cells* Cancer Gene Ther. 2001 April; 8(4):298-307). Said responsive elements have been combined with radiation responsive elements (Greco O. et al., *Novel chimeric gene promoters responsive to hypoxia and ionizing radiation*. Gene Ther 2002; 9: 1403-1411). They may be a part of the replicative or non-replicative adenovirus (Ido A., Uto H., Moriuchi A., Nagata K., Onaga Y., Onaga M., Hori T., Hirono S., Hayashi K., Tamaoki T., Tsubouchi H., *Gene therapy targeting for hepatocellular carcinoma: selective and enhanced suicide gene expression regulated by a hypoxia-inducible enhancer linked to a human alpha-fetoprotein promoter*, Cancer Res. 2001 Apr. 1; 61(7):3016-21; Park J. O., Lopez C. A., Gupta V. K., Brown C. K., Mauceri H. J., Darga T. E., Manan A., Hellman S., Posner M. C., Kufe D. W., Weichselbaum R. R., *Transcriptional control of viral gene therapy by cisplatin*. J Clin Invest. 2002 August; 110(3): 403-10; Cowen R. L., Williams K. J., Chinje E. C., Jaffar M., Sheppard F. C., Telfer B. A., Wind N. S., Stratford I. J., *Hypoxia targeted gene therapy to increase the efficacy of tirapazamine as an adjuvant to radiotherapy: reversing tumor radioresistance and effecting cure*. Cancer Res. 2004 Feb. 15; 64(4):1396-402).

According to the invention, it is also provided a method for expressing foreign DNA in a host cell, which comprises introducing in the host cell a DNA recombinant expression construct or a viral recombinant expression vector of the invention, comprising the promoter molecule of polynucleotide sequence SEQ ID NO 1 operably linked to a foreign DNA encoding a desired polypeptide or RNA, wherein said foreign DNA is expressed.

The introduction of DNA in the host cells may be carried out by means of any construct and includes plasmids, DNA virus, retrovirus, as well as isolated nucleotide molecules. Liposome mediated transfer may also be used.

Adenovirus are an example of said DNA virus that may be used in the present invention. More than 40 different serotypes of human adenovirus are well known, being the Ad5 adenovirus especially preferred as a viral vector in the present invention; however, modified capsid and/or fiber Ad5 adenovirus, such as with the adenovirus 3 capsid or the fiber modification with a RGD motif, are not discarded.

The construction of suitable vectors containing the promoter sequence and the sequence of the desired therapeutic gene may be performed by standard linking and restriction techniques, which are well known in the art. The DNA cleavages in a specific site were performed by treatment with the appropriate restriction enzymes, under conditions indicated by the manufacturer, for approximately 3-16 hs. In general, the restriction results may be verified by electrophoretic separation in agarose gels (0.8-1.6%) in TAE solution (40 mM triacetate, 2 mM $Na_2EDTA.2H_2O$, pH 8.5), using ethidium bromide and visualized with UV light under trans-illuminator (Ultraviolet Products Inc., Upland, Calif.). Ligations are made by DNA ligase from bacteriophage T4, following the manufacturer's protocol (New Englands Biolabs Inc., Beverly, Mass.). Insert:vector ratios of from 1:1 to 3:1 were used, calculating the ratio between the fragments through the following formula:

$$\left[\frac{ng\ vector * Kb\ insert}{Kb\ vector}\right] * \left[ratio\frac{insert}{vector}\right] = ng\ insert.$$

In the vector construction it is advantageous to be able to distinguish the vector incorporating foreign DNA from non-modified vectors by means of a quick assay. Marker systems are known that in general comprise a gene the expression of which confers an identifiable phenotype to the transformed cells when the cells are grown in an appropriate media. The β-galactosidase gene is for instance a detectable gene in clones exhibiting a blue phenotype in plaques with X-gal.

This invention involves driving a gene of interest towards a tumor cell so that the protein encoded by the gene is expressed and said protein directly or indirectly enhances the patient state.

According to a particular embodiment of the invention, a CRAd or oncolytic vector (Conditionally Replicative or Oncolytic Adenovirus) is prepared upon the basis of an adenovirus, comprising a gene of the E1A protein, under the regulation of a DNA sequence fragment of the SPARC promoter. Advantageously, the CRAds of the invention drive the expression of E1A in different types of tumor cells (melanoma, breast, colon, cervix) causing their lysis and elimination through the replication of the virus itself. Also advantageously, the CRAds of the invention containing the E1A gene, such as exemplified below, have attenuated lytic activity in normal cells (mesenchymal, endothelial and fibroblasts) given that its expression is driven by a promoter that expresses mainly in tumor cells.

Also, according to another particular embodiment, CRAd vectors further comprising a suicide gene such as, e.g., Herpes simplex virus thimidine kinase (hsv-TK) codifying for an enzyme capable of phosphorilating the prodrugs acyclovir/ganciclovir. In its phosphorilated form, the anti-herpetic agent is incorporated to the DNA molecule, avoiding its duplication and causing cell death. The CRADs prepared according to this particular embodiment drive hsv-TK expression in different tumor cell types, completing the lytic action and at the same time having an attenuated lytic activity in normal cells given that its expression is driven by a promoter that expresses mainly in tumor cells Also, according to another particular embodiment, CRAd vectors further comprising a genome adenoviral region called E3 codifying for 9 proteins, is prepared. Among them, the ADP (Adenoviral Death Protein) stands out, which promotes the late cellular lysis within the viral infection cycle for allowing the release of mature virions to the cellular microenvironment. The CRAds containing the E3 region potentiate the lytic activity of E1A, at the same time it has an attenuated lytic activity in normal cells given that its expression is driven by a promoter that expresses mainly in tumor cells.

The constructs or vectors of the present invention may be administered to a patient in need thereof, by injection, oral or topic administration, vehiculized in a suitable carrier. Suitable carriers may be aqueous, lipidic, liposomal, etc.

For the data analysis of luciferase, spheroids and in vivo studies, ANOVA variance analysis was used, followed by Tukey's test. A P-value lower than 0.05 was considered significant. Also, the survival curves were performed according to the Kaplan-Meier method and the statistical comparisons between the different groups was performed applying the log-rank test.

The present invention is illustrated below by means of detailed experimental examples. Said examples are intended to provide for a better understanding of the invention, but they should not be deemed to limit the invention in any way, since the scope of the invention shall be established in the annexed claims.

EXAMPLES

Example 1

Evaluation of the Expression of SPARC mRNA in Different Tumor and Normal Lines

The levels of produced messenger RNA (mRNA) from the SPARC protein were assessed by Real-Time PCR in tumor cell lines and normal cell lines.

The human lines HeLa (cervix cancer, ATCC No. CCL-2), T-47D (breast cancer, ATCC No. HTB-133), WI-38 (fetal pulmonary fibroblasts, ATCC No. CCL-75), WI-38 VA (transformed fetal pulmonary fibroblasts, ATCC No. CCL-75.1), HFL-1 (fibroblasts, ATCC No. CCL-153), 293 (embryo kidney, ATCC No. CRL-1573), LoVo (colon cancer, ATCC No. CCL-229), HCT-116 (colon cancer, ATCC No. CCL-247), CaCO2 (colon cancer, ATCC No. HTB-37), HT-29 (colon cancer, ATCC No. HTB-38), T84 (colon cancer, ATCC No. CCL-248) and aortic endothelial cells (Bovine Aortic Endothelial Cells, BAEC ATCC No. CRL1395) were obtained from ATCC (American Tissue Culture Collection, Rockville, Md., USA). The human melanoma cell lines IIB-MEL-LES and IIB-MEL-J-N were previously described by Ledda et. al., 1997; the human melanoma lines SB2, A375N and MEL-888 were kindly provided by Dr. Estela Medrano (Houston, Tex.). All of the cells were cultured in the recommended medium supplemented with 10% bovine fetal serum (provided by Natocor, Carlos Paz, Argentina), 2.5 U/ml de penicillin (Sigma-Aldrich Corp., St. Louis, Mo.) and 2.5 µg/ml streptomycin (Sigma-Aldrich Corp., St. Louis, Mo.) and kept at 37° C. in an atmosphere with 5% $CO_2$. BAEC cells were supplemented with 5% BFS.

The relative quantification of the SPARC mRNA levels was performed according to Pfaffl, M. W. *A new mathematical model for relative quantification in real-time RT-PCR*. Nucleic Acids Res, 29: e45, 2001. Total RNA was extracted by using Tri Reagent (Sigma-Aldrich Co., St. Louis, Mo.). 5 µg of RNA were retro-transcribed with 200 U SuperScript II Reverse Transcriptase (Invitrogen, Carlsbad, Calif.) using 500 ng Oligo(dT) primers. The cDNA Real-Time PCR reaction was performed in an iCycler iQ System (Bio-Rad Laboratories, Hercules, Calif., USA) thermocycler. The reaction was carried out in a 25 µl volume containing 1 Platinum® Taq DNA polymerase (Invitrogen) unit, 1× PCR Reaction Buffer (20 mM Tris-HCl, pH 8.4, and 50 mM KCl), 1.5 mM $Mg_2Cl$, 2.5 µg BSA, 0.01% glycerol, 0.4 µM of each specific primer: SPARC (SRTse; AACCGAAGAGGAGGTGGTG, SEQ ID NO 2/SRTas; GCAAAGAAGTGGCAGGAAGA, SEQ ID NO 3) and β-actin (Acse; AGAAAATCTGGCACCACACC, SEQ ID NO 4/Acas; CAGAGGCGTACAGGGATAGC, SEQ ID NO 5) 200 µM dNTPs and 0.3× SYBR Green solution. The reaction conditions were: 90 seconds at 94° C. and then 30 cycles of 30 seconds at 94° C., 30 seconds at 60° C. and 30 seconds at 72° C. Each reaction was performed in triplicate and the results obtained for SPARC were normalized with the results obtained simultaneously for β-actin.

Figure 2:
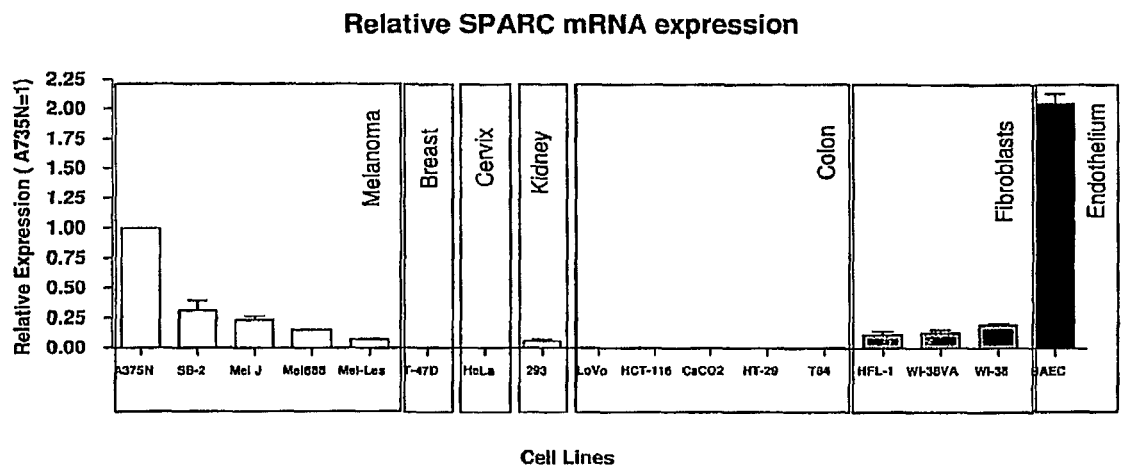
FIG. 2 shows a comparative assessment of the expression levels of SPARC mRNA in different tumor and normal lines.

The results are shown in FIG. 2, wherein it can be seen that the A375N melanoma cells express the higher SPARC mRNA levels. The rest of the melanoma lines express low to moderate mRNA levels compared to A375N. It was observed that the breast (T-47D), cervix (HeLa) and colon (LoVo, HCT-116, CaCO2, HT-29 and T84) cancer lines express negligible SPARC levels. Low SPARC expression levels were observed for the kidney line, while the fibroblasts lines show moderate expression levels and one aortic bovine endothelium line (BAEC) shows a higher SPARC expression level than A375N.

Example 2

Figure 3:
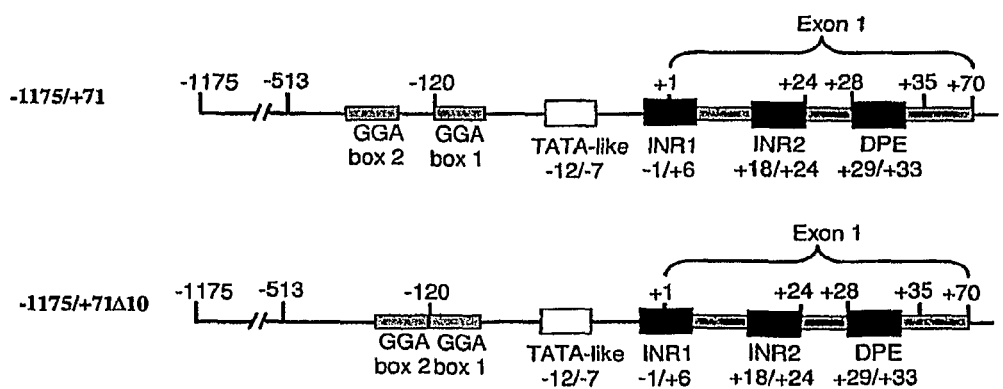

Cloning of 11 Fragments of the Human SPARC Promoter in the PGEM and TOPO Plasmids A sequence analysis of the human SPARC promoter performed by the present inventors revealed a DPE sequence (Downstream Promoter Elements) present between the bases +29/+33 as well as the 2 possible transcription initiation sites which had already been described, INR1 and INR2 (see above cited FIG. 1). The DPE sequence was described in *Drosophila* promoters and is considered to have a role in the transcriptosome assembly in those promoters not containing TATA sequences (Kadonaga, J. T. *The DPE, a core promoter element for transcription by RNA polymerase II*. Exp Mol Med, 34: 259-264, 2002). As a result of this analysis, present inventors carried out a directed mutation of the promoter. For that purpose, they worked on the 5' ends: −1175 (for cloning the complete promoter), −513 (by analogy with the bovine promoter) and −120 (which includes exactly the GGA1 sequence). The 3' end mutations include the complete exon 1 and diverse deletions including, or not, the DPE sequence (+24, +28, +35, +71). FIG. 3 shows two schemes of the SPARC promoter where the different fragments are derived from. The locations of the GGA boxes, the TATA-like sequence of the possible transcription initiation sites (INR) and the DPE sequence are indicated. Different limits are indicated that were used for constructing the SPARC promoter fragments. The 5' end was cloned up to the bases −1175, −513 and −120; while from the 3' end the bases were cloned up to +24, +28, +35 and +71. The deleted region between the GGA boxes is also indicated, this deletion gives origin to the fragment −1175/+71Δ10.

A fragment of 1246 bp from the human SPARC promoter region was amplified by PCR (−1175 to +71 bp relative to the transcription initiation site) from genomic DNA of human lymphocytes with the Spfse and SPP3'2 oligonucleotides (see Table 1). This PCR product, −1175/+71, was cloned in the pGEM-T-easy vector (Promega Corp., Madison, Wis.) for obtaining PGEM (−1175/+71). This plasmid was used as a template of the promoter variants, the fragments of which were in turn amplified by PCR using the primers as detailed in the following Table 1.

TABLE 1

| Fragment | Primer | Enzyme | T mel | 5'-3' Sequence | SEQ ID NO |
|---|---|---|---|---|---|
| −1175/+71 | SPfSE | NheI | T = 64.3 | CTAGCTAGCAGCTGGGTGTTGTGGCAT | 6 |
|  | SPP3'2 | SalI | T = 70.2 | ACGCGTCGACCTCAGTGGCAGGCA | 7 |
| −1175/+71Δ10 | SPfSE | NheI | T = 64.3 | CTAGCTAGCAGCTGGGTGTTGTGGCAT | 6 |
|  | Δ10r | — | T = 75.4 | CGGCCTCCTCCTTCTCCCCTGTC-TCTGTCTTTCATTTC | 8 |
|  | Δ10f | — | T = 65.2 | CTAGCTAGCGGGAGAAGGAGGAGGCC | 9 |
|  | R71 | BglII | T = 59.8 | GCAGATCTCCTCAGTGGCAGGC | 10 |

TABLE 1-continued

| Fragment | Primer | Enzyme | T mel | 5'-3' Sequence | SEQ ID NO |
|---|---|---|---|---|---|
| -1175/+35 | F1175 | MluI | T = 65.2 | GCACGCGTAGCTGGGTGTTGTGG | 11 |
| | R35 | BglII | T = 60.8 | CGAGATCTGCTCTCCGGGCAG | 12 |
| -1175/+28 | F1175 | MluI | T = 65.2 | GCACGCGTAGCTGGGTGTTGTGG | 11 |
| | R28 | BglII | T = 63.1 | CGAGATCTGGGCAGTCTGAAGGACC | 13 |
| -513/+71 | F512 | MluI | T = 63.7 | CGACGCGTGCAGCTTGTCTTGTC | 14 |
| | R71 | BglII | T = 59.8 | GCAGATCTCCTCAGTGGCAGGC | 10 |
| -513/+35 | F512 | MluI | T = 63.7 | CGACGCGTGCAGCTTGTCTTGTC | 14 |
| | R35 | BglII | T = 60.8 | CGAGATCTGCTCTCCGGGCAG | 12 |
| -513/+28 | F512 | MluI | T = 63.7 | CGACGCGTGCAGCTTGTCTTGTC | 14 |
| | R28 | BglII | T = 63.1 | CGAGATCTGGGCAGTCTGAAGGACC | 13 |
| -513/+24 | F512 | MluI | T = 63.7 | CGACGCGTGCAGCTTGTCTTGTC | 14 |
| | R24 | BglII | T = 60.2 | GCAGATCTAGTCTGAAGGACCGCG | 15 |
| -120/+71 | F120 | MluI | T = 60.9 | GAACGCGTGGGAGAAGGAGGAG | 16 |
| | R71 | BglII | T = 59.8 | GCAGATCTCCTCAGTGGCAGGC | 10 |
| -120/+35 | F120 | MluI | T = 60.9 | GAACGCGTGGGAGAAGGAGGAG | 16 |
| | R35 | BglII | T = 60.8 | CGAGATCTGCTCTCCGGGCAG | 12 |
| -120/+28 | F120 | MluI | T = 60.9 | GAACGCGTGGGAGAAGGAGGAG | 16 |
| | R28 | BglII | T = 63.1 | CGAGATCTGGGCAGTCTGAAGGACC | 13 |

The amplification cycle corresponds to an initial denaturalization at 94° C. for 3 minutes, followed by 35 amplification cycles: 94° C., 1 minute, annealing T (variable, depending on each product, Table 1), 1 minute and 72° C. 2 minutes, followed by a final extension at 72° C. for 10 minutes. The PCRs were performed in the PTC-200 thermocycler (MJ Research Inc., Whaltam, Mass.).

The PCR products were firstly cloned in the pGEM-t-easy vector (Promega Corp., Madison, Wis.) or TOPO-pCR4 vector (Invitrogen Corp., Carlsbad, Calif.) thus obtaining the vectors:

a—pGEM (−1175/+71), (SEQ ID NO 17), complete promoter. The sequence +1/+70, includes the first exon, not translated.

b—pGEM (−1175/+71Δ10) (SEQ ID NO 18). This promoter is a modification of the complete SPARC promoter −1175/+71, wherein a sequence of 10 bp considered to inhibit transcription was deleted, located between the two GGA boxes (Hafner, M. et al., 1995). For this purpose, the splicing by overlap extension PCR (PCR-SOE) was applied using two SPARC promoter fragments that had been previously cloned by the present inventors: Spdel1.1 Kb of 1084 base pairs and GGA1 of 209 base pairs. The final PCR product was cloned in the PGEM vector and the deletion was confirmed by sequencing.

c—TOPO (−1175/+35), (SEQ ID NO 19), includes the DPE sequence d—TOPO (−1175/+28), (SEQ ID NO 20), excludes the DPE sequence e—TOPO (−513/+71), (SEQ ID NO 21), includes the complete first exon.

f—TOPO (−513/+35), (SEQ ID NO. 1), includes the DPE sequence g—TOPO (−513/+28), (SEQ ID NO. 22), excludes the DPE sequence h—TOPO (−513/+24), (SEQ ID NO 23), includes up to the INR2 sequence i—TOPO (−120/+71), (SEQ ID NO 24), includes the complete first exon.

j—TOPO (−120/+35), (SEQ ID NO 25), includes the DPE sequence k—TOPO (−120/+28), (SEQ ID NO 26), excludes the DPE sequence Example 3A Selection of a Fragment of the Human SPARC Promoter The promoters obtained according to Example 2 were subcloned in the MluI/BglII, MluI/XhoI or NheI/XhoI sites of the pGL3-Basic plasmid (Promega Corp., Madison, Wis., USA) upstream of the luciferase reporter gene. All of the clonings was confirmed by restriction profiles and by sequencing the vectors (pGEM, TOPO and/or pGL3) with the universal primers T7 (TACGACTCACTATAGGG; SEQ ID NO 27); Sp6 (ATTTAGGTGACACTATAG; SEQ ID NO 28), T3 (ATTAACCCTCACTAAAGGGA; SEQ ID NO 29) or P2 (CTTTATGTTTTTGGCGTCTTCCA; SEQ ID NO 30) and P3 (CTAGCAAAATAGGCTGTCCCC; SEQ ID NO 31).

The pGL3-Basic plasmid contains the modified Firefly luciferase reporter gene (luc+) for preventing the binding of genic regulatory factors, removing the restriction sites, preventing the protein transport to peroxisomas and it contains a Kozak sequence in the 5' end of the luciferase gene for optimizing the translation efficiency.

The presence of the luciferase reporter gene allowed for the quantification of SPARC promoter activity in the 11 fragments obtained in Example 2, by measuring the luciferase enzymatic activity. The assay was performed in three cell lines, using the (melanoma) A375N line as a model since it expresses high SPARC levels and the (cervix) HeLa and (breast) T-47D lines, not expressing SPARC, according to the teachings of Example 1 above.

The cells were seeded in 24-well plates with a density of $4 \times 10^4$ cells/well. After 24 hours they were transfected using Lipofectamine2000 (Invitrogen Corp., Carlsbad, Calif.) according to the conditions indicated by the manufacturer. Each treatment was carried out at least in duplicate for each cell line, incubating 0.8 µg of treatment plasmid with 0.1 µg of pRL-CMV plasmid for 5 minutes with 50 µl DMEM medium without antibiotic and simultaneously, 1 µl Lipofectamine2000 with 50 µl of the same medium. These two preparations were mixed and incubated for 20 minutes at room temperature. The medium with cell serum was removed, washed with PBS and 200 µl high glucose DMEM was added without serum and without antibiotics; subsequently, 100 µl medium containing the lipofection mixture was added and 800 µl of culture medium corresponding to each cell line, supplemented with BFS, was added 4 hours later. The cells used were kept in a stove for 46 hours at 37° C. with 5% $CO_2$. The Dual Luciferase Reporter Assay System kit (Promega Corp., Madison, Wis.) was used for the luciferase assay. This system implies the simultaneous expression of two individual reporter enzymes in the same system, allowing for the evaluation of the activity produced by the luciferase enzymes from the Firefly glow-worm (*Photinus pyralis*) and the *Renilla coelenterate* (*Renilla reniformis*) in only one sequential assay (Sherf, B. A. et al., *Dual Luciferase Reporter Assay: An Advanced Co-Reporter Technology Integrating Firefly and Renilla Luciferase Assays*. Promega Notes Magazine: 2-9, 1996). The data were normalized in the following way:

$$\frac{\text{Firefly Luciferase Units}}{\text{Renilla Luciferase Units}} = \text{Relative Luciferase Units} (RLU)$$

Figure 4:
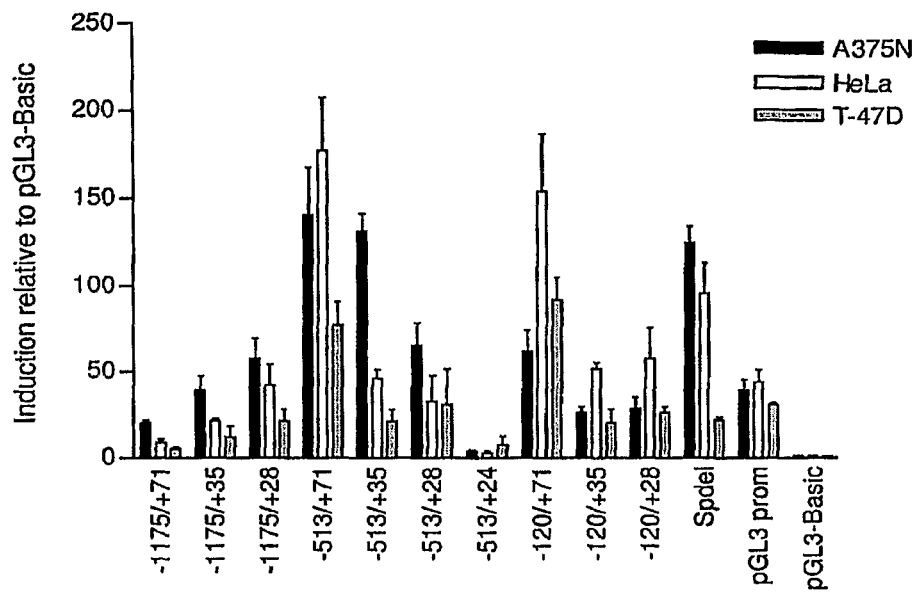
FIG. 4A shows the promoter activity of 11 fragments of the SPARC promoter by measuring the enzymatic activity of the Luciferase reporter gene in A375N (melanoma), HeLa (cervix) and T-47D (breast) cell lines.
FIG. 4B compares the promoter activity of the fragments −513/+35 (F512) and −1175/+71Δ10 (Spdel) of the SPARC promoter by measuring the enzymatic activity of the Luciferase reporter gene in various normal and tumor cell lines.
Figure 4:
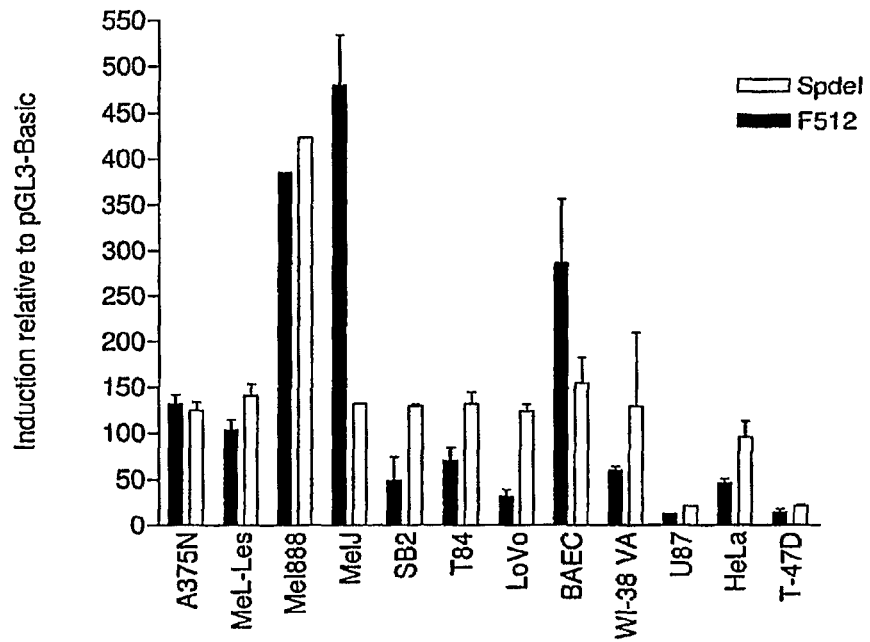

The data are expressed as induction amount relative to the activity obtained with the pGL3-Basic control plasmid (without promoter). The results are shown in FIG. 4A. The pGl3-promoter plasmid (pGL3-prom, Promega Corp., Madison, Wis.) wherein the viral promoter from SV40 drives the expression of the luciferase enzyme, was used as a transfection control.

The lower promoter activity in melanoma lines was observed with the complete SPARC promoter (−1175/+71). The higher unspecificity was observed with the fragment −120/+71 and the fragment showing the higher specificity and higher activity in the line expressing SPARC turned out to be the fragment −513/+35 (FIG. 4A). The promoter −513/+35, from now onwards F512, was selected through this analysis in order to continue with its characterization in comparison to the promoter −1175/+71Δ10, called Spdel given that it had the same activity than F512, in the A375N melanoma line.

Example 3B

Selection of a Fragment from the Human SPARC Promoter

The two promoters F512 and Spdel, having similar promoter activity and as identified by the method of Example 3A, were assessed in different tumor and normal cell lines (see references in Example 1). The results are shown in FIG. 4B.

From the comparative results, it can be noted that Spdel presents an average of 140 times higher activity, with respect to the empty vector pGL3-Basic, both in tumor and normal lines, with the exception of the melanoma line MEL888, where its activity is 430 times higher (FIG. 4B). Hence, the Spdel activity results independent of SPARC expression in the cell line used.

The F512 promoter turned out to be active in the melanoma lines and in the endothelium BAEC line having the higher SPARC expression. The SB2 line has the lower promoter activity, approximately ⅓ of the activity observed in A375N, this result being coincident with the SPARC mRNA expression ratio (FIGS. 2 and 4B). Surprisingly, the activity in two melanoma lines, Mel888 and MelJ, is 3.5- to 4-fold higher than for A375N. These results show that the F512 fragment is active in the melanoma lines but its behavior is not always coincident with the SPARC mRNA expression. Unlike Spdel, which has the same activity in all lines, F512 presents lower activity in those lines with little or null SPARC expression such as colon (T84, LoVo), glioma (U87) or cervix (HeLa) (FIG. 4B). However, this activity is not negligible but, quite on the contrary, in a few cases like T84, it reaches half the activity observed for the melanoma lines. In addition, the promoter is also active in the fibroblast line used (WI-38 VA).

These results allowed for the selection of the F512 promoter for driving the expression of genes of interest in an adenovector.

Example 4

Construction of a Shuttle Plasmid Containing F512 Upstream of E1A Gene

The construction of a shuttle plasmid containing the genes of interest was carried out starting from pADPSY shuttle vector, containing the human adenovirus type 5 whose genes in regions E1 (necessary for its replication) and E3, had been deleted. Then, Rous sarcoma virus (RSV) promoter and the polyadenilation signal of SV40 (Mariano J. Alvarez, Federico Prada, Edgardo Salvatierra, Alicia I. Bravo, Viviana P. Lutzky, Cecilia Carbone, Fernando J. Pitossi, H. Eduardo Chuluyan and Osvaldo L. Podhajcer; *Secreted Protein Acidic and Rich in Cysteine Produced by Human Melanoma Cells Modulates Polymorphonuclear Leukocyte Recruitment and Antitumor Cytotoxic Capacity;* Cancer Research 65, 5123-5132, Jun. 15, 2005) have been inserted in ΔE1 region. In order to improve this vector so as to increase the variety of unique cloning sites, a multiple cloning site (MCS) was designed and included, replacing RSV promoter, obtaining pAd-Xp plasmid (SEQ. ID. NO 32); this vector was sequenciated in order to verify the presence of the multiple cloning site.

In the last years many studies showed that primers that were specific for a given cell type, did not act as such when they were introduced in the viral genome (Steinwaerder, D. S. and Lieber, A. *Insulation from viral transcriptional regulatory elements improves inducible transgene expression from adenovirus vectors in vitro and in vivo*. Gene Ther, 7: 556-

567, 2000.). This is due to the fact that ITR sequences (inverted terminal repetitions) and the adenovirus genome encapsulation signal have enhancers influencing the promoters activity modifying their specificity (Hearing, P. and Shenk, T. *The adenovirus type 5 E1A enhancer contains two functionally distinct domains: one is specific for E1A and the other modulates all early units in cis*. Cell, 45: 229-236, 1986.). This problem can be partially avoided by the use of insulators, i.e. sequences that isolate the promoter activity and allow it to develop its specificity (Steinwaerder, D. S. et al., 2000; Martin-Duque, P., Jezzard, S., Kaftansis, L., and Vassaux, G. *Direct comparison of the insulating properties of two genetic elements in an adenoviral vector containing two different expression cassettes*. Hum Gene Ther, 15: 995-1002, 2004.). From these findings the present inventors decided to clone, in the pAd-Xp shuttle vector MCS, an insulator sequence (the stop signal of the bovine growth hormone) (Martin-Duque, P. et al., 2004)) yielding new pAd(I)-Xp shuttle vector (SEQ. ID. NO 33). The insulator sequence was amplified by PCR using the INSU-F-SpeI (CCACTAGT-GCTAGAGCTCGCTGATCAGC; SEQ. ID. NO 34) and INSU-R-KpnI (CGGTACCATCCCCAGCATGCCTGC; SEQ. ID. NO 35) primers. The product of this reaction was cloned in TOPO-pCR4 (Invitrogen Corp., Carlsbad, Calif.) and subsequently subcloned in SpeI and KpnI sites of pAd-Xp, yielding pAd(I)-Xp.

The cDNA of E1A protein was cloned by PCR starting from the genomic DNA of 293 human embryo kidney cells (ATCC No. CRL-1573) that constitutively express it. A fragment corresponding to 560-1632 nucleotides of the virus genome was amplified by PCR. This fragment was cloned in TOPO-pCR4 (SEQ ID NO 36 and SEQ ID NO 37) vector and sequenced in order to verify the identity of the sequence. The constructs were subcloned in pcDNA3 expression vector and expressed in HeLa cells. A Western Blot of proteins from the complete lysate was carried out and they could be identified with anti-E1A antibody (BD Pharmigen, #554155).

In a first step, E1A protein gene was cloned in pAd(I)-Xp and pAd-Xp vectors. For that purpose, the E1A protein cDNA was extracted from TOPO-pCR4-E1A vector (SEQ IND NO 36) with BglII and BamHI enzymes and was inserted in BglII site of pAd(I)-Xp and pAd-Xp yielding pAd(I)-Xp-E1A (SEQ. ID. NO 38) and pAd-Xp-E1A (SEQ. ID. NO 39). In a second step F512 was extracted from pGL3(−513/+35) with MluI and BglII and it was cloned in MluI and BglII sites of pAd(I)-Xp-E1A and pAd-Xp-E1A, leaving the E1A protein cDNA downstream of F512. Thus, pAd(I)-F512 (SEQ. ID. NO 40) and pAd-F512 (SEQ. ID. NO 41) vectors were obtained; both vector sequences were confirmed by sequenciation with pAd-sense (TGTTTTTCTCAGGT-GTTTTCCG; SEQ. ID. NO 42) primer.

Example 5

Construction of a Shuttle Plasmid Containing F512 Upstream of hsv-TK Suicide Gene cDNA coding for hsv-TK was amplified by PCR using as template the DNA of pAGO plasmid (Berenstein, M., Adris, S., Ledda, F., Wolfmann, C., Medina, J., Bravo, A., Mordoh, J., Chernajovsky, Y., and Podhajcer, O. L. *Different efficacy of in vivo herpes simplex virus thymidine kinase gene transduction and ganciclovir treatment on the inhibition of tumor growth of murine and human melanoma cells and rat glioblastoma cells*. Cancer Gene Ther, 6: 358-366, 1999) and FTK/RTK (GCCCATGGCTTCGTACCCCGGCC; SEQ. ID. NO 43/GCGTCGACTCAGTTAGCCTCCCCCATCTC; SEQ. ID. NO 44) primers. The product of this PCR reaction was cloned in TOPO-pCR4 vector. The obtained TK-TOPO-pCR4 plasmid (SEQ. ID. NO 45) was confirmed by digestion with restriction enzymes and by sequenciation using T3 (AT-TAACCCTCACTAAAGGGA; SEQ. ID. NO 29) and T7 (TAATACGACTCACTATAGGG; SEQ. ID. NO 27) universal primers.

The cDNA of hsv-TK enzyme was extracted from TK-TOPO-pCR4 plasmid (SEQ ID NO 45) by enzymatic digestion with NcoI and SalI. This NcoI-TK-SalI fragment was cloned in pCITE vector (Invitrogen, Carlsbad, Calif.) downstream of a internal ribosomal entry site (IRES) allowing for a greater translation efficiency without capping. The resulting pCITE-TK vector was confirmed by digestion with restriction enzymes. Subsequently, the IRES-TK fragment of the pCITE-TK vector was extracted by digesting with EcoRI and SalI enzymes. EcoRI site was filled with Klenow enzyme and the IRES-TK-SalI fragment was subcloned in pAd(I)-FS12 vector obtained in Example 4, previously digested with EcoRV and SalI enzymes. The obtaining of the resulting vector from said cloning, pAd(I)-F512-TK (SEQ ID NO 46 and SEQ ID NO 47), was confirmed by digestion with restriction enzymes and sequenciation with pAd-sense (TGTTTTTCTCAGGTGTTTTCCG; SEQ. ID. NO 42) and pAd-antisense (CACAAATTTCACAAATAAAGCATTT; SEQ. ID. NO 48) primers.

Example 6

Construction of a Shuttle Plasmid Containing F512 Upstream of the Gene Coding for EGFP Green Protein The EGFP protein cDNA linked to an IRES sequence at its 5' end was extracted from pDC315-iGFP plasmid (modified plasmid from pDC315 commercial plasmid from Microbix Biosystems Inc., Toronto, Ontario, Canada) by digestion with EcoRI and SalI enzymes. The EcoRI site was filled with Klenow enzyme and the IRES-EGFP-SalI fragment was subcloned in the pAd(I)-F512 vector obtained according to what is disclosed in Example 4, previously digested with EcoRV and SalI enzymes. The obtaining of the vector resulting from this cloning, pAd(I)-F512-EGFP (SEQ ID NO 49 and SEQ ID NO 50), was confirmed by digestion with restriction enzymes and sequenciation with pAd-sense (TGTTTTTCT-CAGGTGTTTTCCG; SEQ ID NO 42) and pAd-antisense (CACAAATTTCACAAATAAAGCATTT; SEQ ID NO 48) primers.

Example 7

Obtaining of Ad-F512 Recombinant Virus

Figure 5:
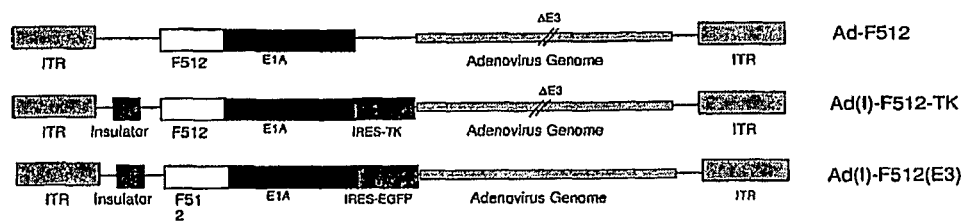
FIG. 5A shows schemes of Ad-F512, Ad(I)-F512-TK and Ad(I)-F512(E3) adenoviruses, constructed according to the present invention.
FIG. 5B shows the restriction profile of Ad-F512, Ad(I)-F512-TK and Ad(I)-F512(E3) adenoviruses of the present invention with HindIII enzyme.
Figure 5:
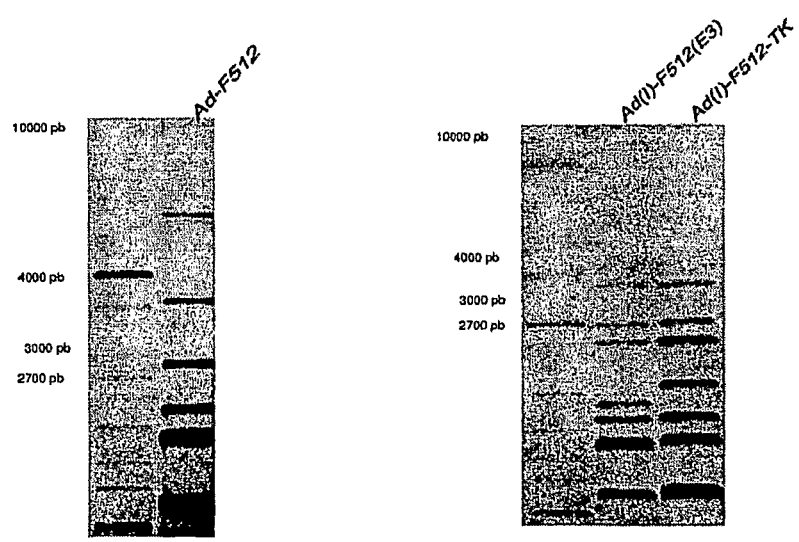

The pAd-F512 plasmid (SEQ ID NO 41) obtained according to what is disclosed in Example 4, was linearized with FspI enzyme and cotransfected together with a adenovirus type 5 fragment previously restricted with ClaI enzyme, including from mu 2.6 to mu 100 with deletion in E3 region. Cotransfection was carried out in 293 cells by means of calcium phosphate (Ferrari, C. C., Depino, A. M., Prada, F., Muraro, N., Campbell, S., Podhajcer, O., Perry, V. H., Anthony, D. C., and Pitossi, F. J. *Reversible demyelination, blood-brain barrier breakdown, and pronounced neutrophil recruitment induced by chronic IL-1 expression in the brain*. Am J Pathol, 165: 1827-1837, 2004) and according to Nevins et al. protocol in 293 cells (Nevins, J. R. *Definition and mapping of adenovirus 2 nuclear transcription*. Methods Enzymol, 65: 768-785, 1980). By homologous recombination between the adenoviral regions of the two transfected fragments Ad-F512 (SEQ ID NO 51 and SEQ ID NO 52) the recombinant adenovirus was obtained. An Ad-F512 constructed adenovirus scheme is shown in FIG. 5A.

Once obtained, the Ad-F512 recombinant adenovirus was cloned and a stock purification was made by means of a cesium chloride double gradient (Lieber, A., He, C. Y., Kirillova, I., and Kay, M. A. *Recombinant adenoviruses with large deletions generated by Cre-mediated excision exhibit different biological properties compared with first-generation vectors in vitro and in vivo*. J Virol, 70: 8944-8960, 1996). The adenovirus preparation was titrated by means of DICT50 (Lieber, A. et al., 1996) in 293 cells obtaining $10^{12}$ vp/ml for Ad-F512. Ad5-wt was included as a positive replication control in the assay, obtaining a preparation therefrom the title of which was 6, $8\times10^{11}$ vp/ml.

Besides, in order to confirm the identity of the viral stock, a viral DNA preparation was made, which was used to be digested with restriction enzymes and to be sequenciated using pAd-sense (TGTTTTTCTCAGGTGTTTTCCG; SEQ ID NO 42) and pAd-antisense (CACAAATTTCA-CAAATAAAGCATTT; SEQ ID NO 48) internal primers, (See FIG. 5B).

Example 8

Obtaining of the Ad(I)-F512-TK Recombinant Virus

In a similar way as described in Example 7, the pAd(I)-F512-TK (SEQ ID NO 46 and SEQ ID NO 47) plasmid obtained in Example 5, was linearized with FspI enzyme and cotransfected together with a Ad5 fragment, previously restricted with ClaI enzyme, including from mu 2.6 to mu 100, with deletion in region E3. Cotransfection was carried on in 293 cells by means of the calcium phosphate method (Ferrari, C. C. et al.; 2004) and according to Nevins' protocol in 293 cells (Nevins, J. R.; 1980). By homologous recombination between adenoviral regions of the two cotransfected fragments, the Ad(I)-F512-TK (SEQ ID NO 53 and SEQ ID NO 54) recombinant adenovirus was obtained. A scheme thereof is shown in FIG. 5A.

Once obtained, the Ad(I)-F512-TK adenovirus was cloned and a stock purification was made by means of a cesium chloride double gradient (Lieber, A. et al.; 1996). The adenovirus preparation was titrated by means of DICT50 (Lieber, A. et al., 1996) in 293 cells yielding a titer of $10^{12}$ vp/ml. Ad5-wt was included as a positive replication control in the assay, obtaining a preparation therefrom the title of which was 6,8×$10^{11}$ vp/ml.

Besides, in order to confirm the identity of the viral stock, a viral DNA preparation was made, which was used to be digested with restriction enzymes and to be sequenciated using pAd-sense (TGTTTTTCTCAGGTGTTTTCCG; SEQ ID NO 42) and pAd-antisense (CACAAATTTCA-CAAATAAAGCATTT; SEQ ID NO 48) internal primers, (See FIG. 5B).

Example 9

Obtaining of the Ad(I)-F512(E3) Recombinant Virus

The pAd(I)-F512-EGFP plasmid (SEQ ID NO 49 and SEQ ID NO 50) obtained in Example 6, was linearized with FspI enzyme, like in Examples 7 and 8, but in this case the cotransfection was carried out together with another plasmid, JM17 (Microbix Biosystems Inc., Toronto, Ontario, Canada) containing the whole Ad5 genome, except for the E1 region, but containing the E3 region. The cotransfection was carried out in 293 cells by means of calcium phosphate method (Ferrari, C. C. et al.; 2004) and according to the Nevins' protocol in 293 cells (Nevins, J. R.; 1980). By homologous recombination between the adenoviral regions of the two cotransfected fragments, the Ad(I)-F512(E3) (SEQ ID NO 55 and SEQ ID NO 56) recombinant adenovirus was obtained, the scheme of which is shown in FIG. 5A, and that contains the E3 region of the original virus (Ad5).

Once obtained, the recombinant adenovirus containing the E3 region was cloned and the stock was purified by means of a double cesium chloride gradient (Lieber, A. et al., 1996). The adenovirus preparation was titrated by means of DICT50 (Lieber, A. et al., 1996) in 293 cells, obtaining a titer of 1,5×$10^{12}$ vp/ml. As a positive replication control in the assay, Ad5-wt was included, obtaining a preparation therefrom the title of which was 6,8×$10^{11}$ vp/ml.

Besides, in order to confirm the identity of the viral stock, a viral DNA preparation was carried out, which was used to be digested with restriction enzymes and to be sequenciated using pAd-sense (TGTTTTTCTCAGGTGTTTTCCG; SEQ ID NO 42) and pAd-antisense (CACAAATTTCA-CAAATAAAGCATTT; SEQ ID NO 48), internal primers (see FIG. 5B).

Example 10

In Vitro Assays with Ad-F512, Ad(I)-F512-TK and Ad(I)-F512(E3) Adenoviruses for the Determination of Cell Infectivity For in vitro assays the adenoviruses obtained in Examples 7, 8 and 9 were used. The cell lines used have already been disclosed in Example 1.

The viruses used in the present invention are based on AdS, the entrance via of which is through CAR receptor. (coxsackie-adenovirus receptor) and integrins (Kanerva, A. and Hemminki, A. *Adenoviruses for treatment of cancer*. Ann Med, 37: 33-43, 2005). Given that the CAR expression is heterogeneous, translation assays were made in different cell lines with a non-replicative adenovirus expressing β-galactosidase enzyme (Ad-β-gal).

The different tumor and normal lines were infected at different multiplicities of infection (MOI) with Ad-β-gal, and the infection percentage was registered (see Table 2). After 3 days an assay with X-gal was carried out in order to reveal β-galactosidase. Blue cells were counted (infected cell indicator) and the percentage regarding non-infected cells was calculated. At least three different fields were counted.

TABLE 2

| | % infection | | | | | | | |
|---|---|---|---|---|---|---|---|---|
| MOI | A375N | HeLa | LoVo | T84 | SB2 | WI-38 | WI-38 VA | BAEC |
| 1 | 0.03125 | 0.25325 | 0.006 | 0.0215 | 5.833333 | 0.02 | 0.24 | 0.0266 |
| 10 | 3.05 | 7.5 | 0.0095 | 0.64 | 27.9 | 0.41 | 2.86 | 0.85 |
| 100 | 27.675 | 21.5 | 2.15 | 10 | 95.2 | 24.69 | 20.5 | 13.9 |

TABLE 2-continued

| | | | | % infection | | | | |
|---|---|---|---|---|---|---|---|---|
| MOI | A375N | HeLa | LoVo | T84 | SB2 | WI-38 | WI-38 VA | BAEC |
| 500 | 35.33333 | 77 | 32.5 | 80.5 | NA | 60.35 | 75.25 | 52.6 |
| 1000 | 53.33333 | 84.75 | 73.33334 | 85 | NA | 91 | 79.65 | 55.94 |

It was noted that, at a multiplicity of infection (MOI) of 1000, almost all of the lines are infected at least in a 75%, excepting those of BAEC and A375N cells, which are only infected in a 50%. At a MOI lower than 100 a low cell infectivity is observed (about 25%) excepting the SB2 melanoma line having an infectivity of more than 95%. At a MOI of 10 almost no infected cells can be seen in any line, but the SB2.

Summarizing, the infection capability of the tested cell lines would be SB2>T84>HeLa>WI-38VA>WI-38>LoVo>BAEC>A375N.

Example 11

In Vitro Assays with Ad-F512, Ad(I)-F512-TK and Ad(I)-F512(E3) Adenovirus for the Assessment of Oncolytic Capability In order to test the oncolytic capability of the adenovirus (CRAds) constructed according to the present invention, they were used to infect in vitro cells having different levels of SPARC expression. Particularly, they were used SB2 melanoma, A375N and MelJ lines; WI-38, WI-38 VA and HFL-1 fibroblasts lines; T84 and LoVo colon lines; HeLa cervix line; BAEC endothelial line; and normal mesenchymal cells. The Ad5-wt (wild type) was used as control. The different tumor lines were infected with Ad-F512 (SEQ ID NO 51 and SEQ ID NO 52), Ad(I)-F512-TK (SEQ ID NO 53 and SEQ ID NO 54), Ad-(I)F512(E3) (SEQ ID NO 55 and SEQ ID NO 56) and Ad5-wt adenoviruses. The adenoviruses lytic effect was assessed by staining with violet crystal the cells that remained attached to the plate after the experiment and through the quantification of the metabolic activity by means of the MTT assay.

Figure 6:
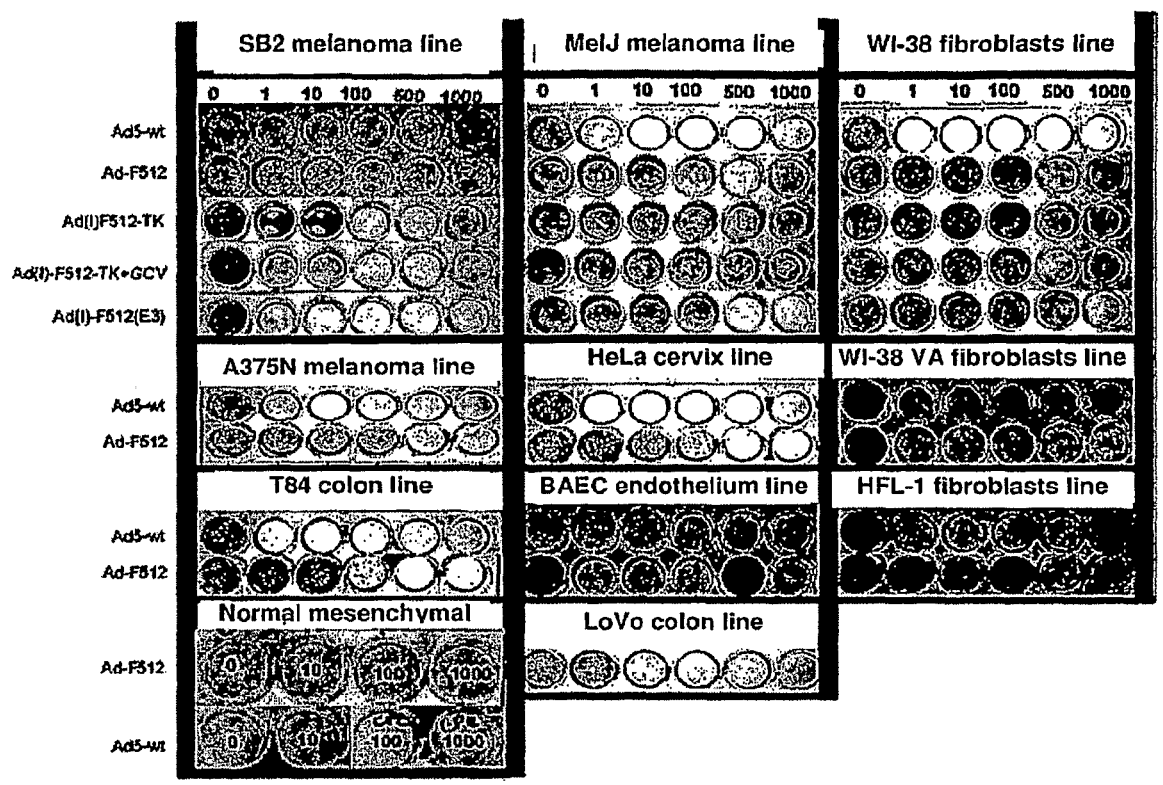
FIG. 6 shows the monolayer cytopathic effect in different tumor lines of Ad-F512, Ad(I)-F512-TK and Ad(I)-F512(E3) adenoviruses, constructed according to the present invention, using Ad5-wt as a control.

The lytic effect of adenoviruses was assessed by staining with violet crystal: Referring to FIG. 6, the monolayer infection proceeding for the study of the cytopathic effect is as follows: the cells were seeded in 24-well plates at a density of 1×10$^4$ cells/well. The following day they were infected in 200 µl of high glucose DMEM 2% BFS during 3 hours at different multiplicities of infection (MOIs). After the infection 800 µl of the corresponding medium for each cell line were added. Ten days later the cells were stained with violet crystal (solution 0.75% in 40% methanol) or stained with β-galactosidase, and in this last case two or more fields were counted in order to register the infection percentage. FIG. 6 shows a photograph of the assay of staining with violet crystal in plate, for the different cell lines employed.

Figure 7:
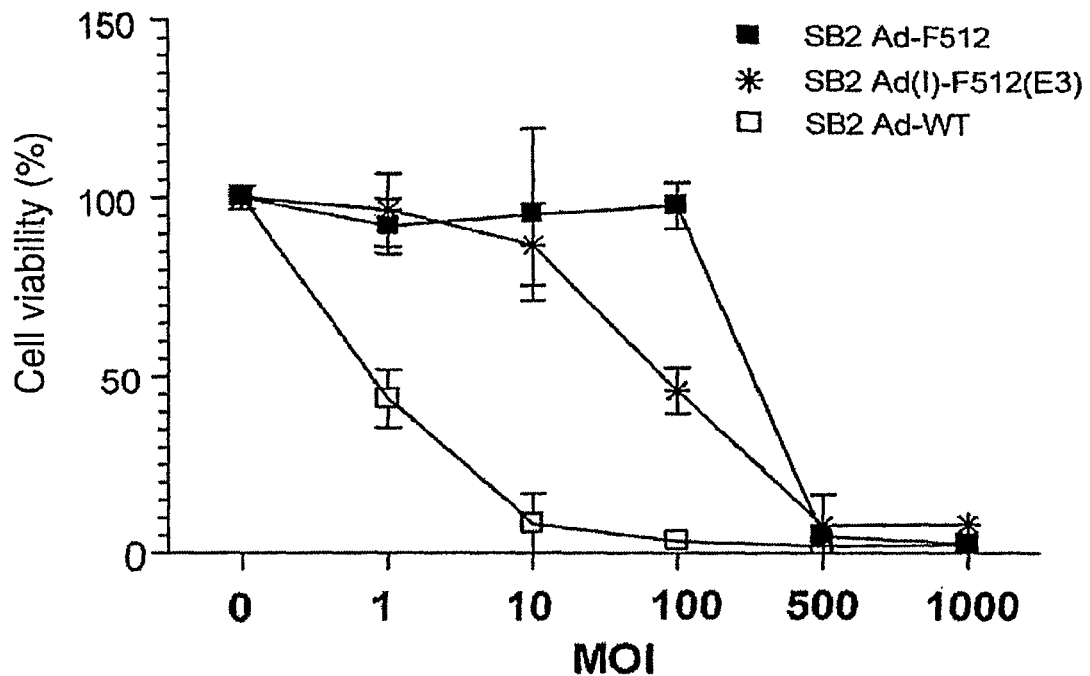
FIGS. 7A, 7B, 7C and 7D show the monolayer lytic effect (MTT assay) of Ad-F512 and Ad(I)-F512(E3) adenoviruses of the present invention, at different MOIs 10 days after infection; A—Melanoma, SB2 cells; B—Melanoma, Mel-J cells; C—Colon cells; D—Breast cells.
Figure 7:
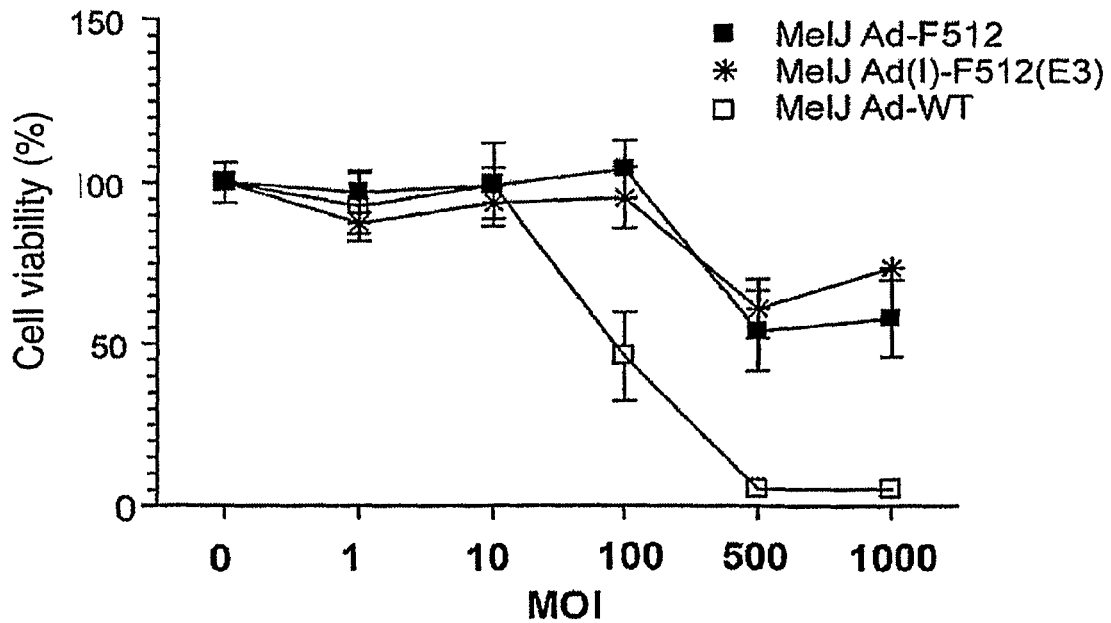
Figure 7:
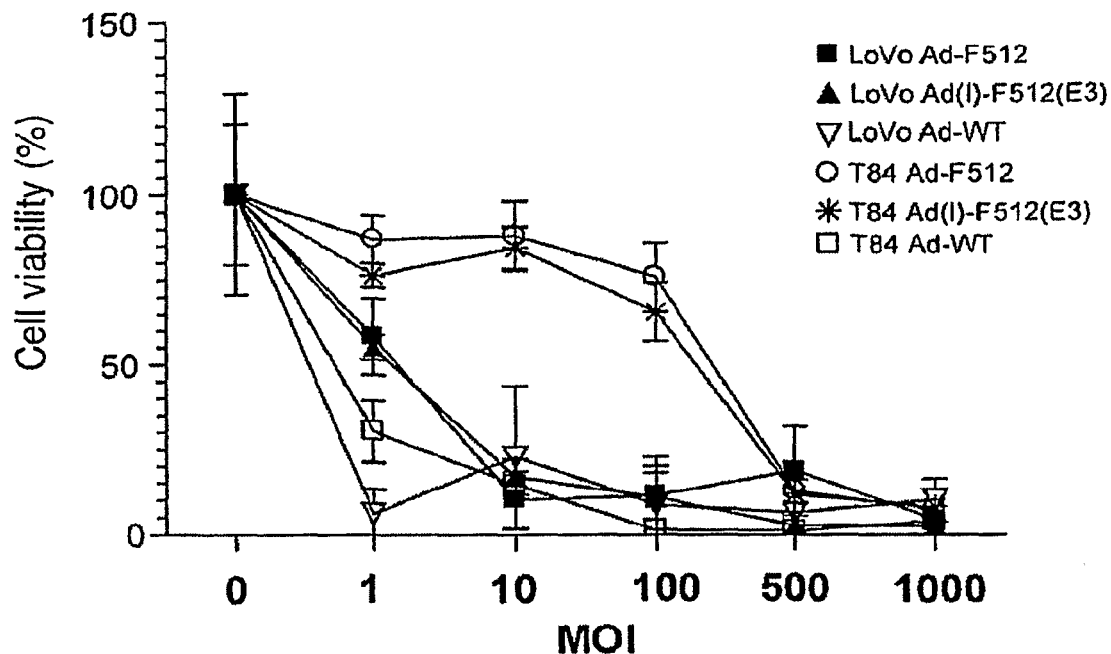
Figure 7:
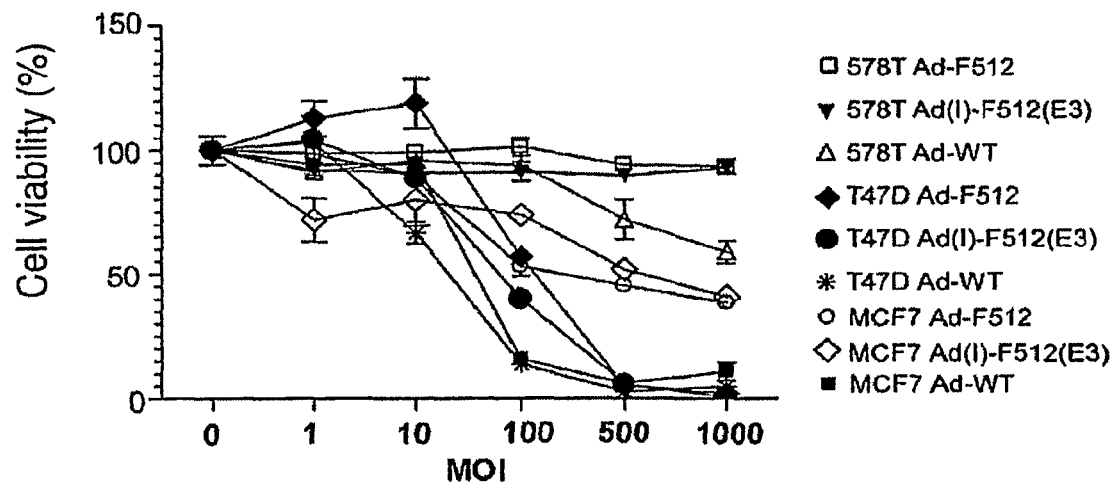

The lytic effect of the adenoviruses was assessed through quantification of metabolic activity by means of MTT assay: The MTT assay (cell viability) is based on the cleavage of the yellow tetrazolium salt in a purple compound (formazan). This reaction only takes place in metabolically active cells having succinate-tetrazolium reductase enzyme present in the mitochondria respiratory chain. The lytic effect measured as a function of metabolic activity (MTT assay) is shown in FIG. 7. In this assay 96-well plates were seeded at a density of 5×10$^3$ cells/well and the following day they were infected during 2 hours in 25 µl (high glucose DMEM 2%). After 2 hours 100 µl of the corresponding medium for each cell line were added. Ten days later the cell viability was accounted by means of the MTT method (Mosmann, T. *Rapid colorimetric assay for cellular growth and survival: application to proliferation and cytotoxicity assays*. J Immunol Methods, 65: 55-63, 1983).

The viability assays with MTT are shown in FIG. 7. Generally, a lytic activity is noted for the various cell types similar to the one shown through violet crystal; but in this case a greater viability was noted for each MOI than those of the corresponding staining with violet crystal. In these assays three lines of breast cancer (578T, MCF7 and T-47D) were included, all of them with very low SPARC expression, and in the case of T-47D with low F512 activity. Surprisingly, two lines (MCF7 and T-47D) turned out to be susceptible to the CRAds at a MOI of 100.

Surprisingly, all of the tumor cells were lysed by the CRAds. However, the lytic activity of the CRAds in the tumor cells turned out to be independent of the SPARC mARN expression degree or of the promoter activity in the cell line. Thus, e.g., for melanoma cells, all of the viruses resulted more effective in SB2 than in MelJ or A375N. This result is coincident with the cell infectivity but not with the promoter activity or with the SPARC expression. Given that the viruses have different infection capability in each line, the comparison between the different viruses was made mainly within the same cell line. In the first place, SB2 is lysed more effectively with Ad(I)-F512(E3)>Ad-F512~Ad(I)-F512-TK±GCV, while in MelJ (wherein the promoter showed a much higher activity) Ad(I)-F512(E3)~Ad-F512>Ad(I)-F512-TK±GCV.

From this comparison it is clear that the less powerful virus is that which has got included the insulator sequence, and that the addition of the E3 region makes the lysis more effective. Besides, no increase of the lytic effect is noted upon adding GCV to the cell culture infected with Ad(I)-F512-TK.

On the other hand, it was noted that T84 colon and LoVo lines turned out to be very susceptible to Ad-F512. In the case of LoVo this effect is stronger than the one observed for SB2 melanoma cells. It can be noted that Ad-F512 was capable of lysing the WI-38 fibroblasts (which express SPARC protein in a moderate way), at a MOI of 500, while the two viruses having an insulator sequence between the virus ITR and the promoter, turned out to be lytic at a MOI of 1000. The addition of GCV slightly increases the lytic capability of Ad(I)-F512-TK. Two additional fibroblast lines—WI-38VA and HFL-1—analyzed with Ad-FS12 virus were poorly lysed at a MOI of 1000. In the three fibroblast lines, Ad5-wt was capable of lysing at a MOI of 1. The endothelial cells were not susceptible to Ad-F512, independently of their high SPARC expression. Primary mesenchymal cells derived from the marrow bone were not affected by Ad-F512 but by Ad5-wt, at a MOI of 100.

As a conclusion, F512 within three adenovectors turns out to be lytic in the most part of tumor lines, while it does not affect normal cells like mesenchymal and endothelial cells and some fibroblasts.

Example 12

Virus Yield in Different Cell Lines

In order to assess the capability of replication of CRAds in different tumor lines, an assay on virus yield was carried out. The results thereof are shown in FIG. 8.

The general proceeding for the virus production in different cell lines is disclosed below:

On day 0, 100000 cells were seeded in each well of a 6-well plate. On day 1 cells were infected at a 50 MOI in a volume of 300 µl per well in high glucose DMEM medium 2% BFS. The infection was carried out during 1 hour at 37° C. with at least two stirring operations. Subsequently, the medium was removed, washed twice with PBS and 1 ml of 10% BFS medium was added. After three days, cells were kept at room temperature for 15 minutes and were picked up together with the medium. The supernatant was placed into an Eppendorf tube and three freezing/thawing cycles were made using liquid nitrogen. Subsequently, it was centrifuged at 4500 rpm and $1/10$ serial dilutions of said supernatant were made in high glucose DMEM medium 5% BFS and 0.01M HEPES. 100 µl of each dilution were seeded (sextuplicate) in a well of a 96-well plate that was seeded the day before with 293 cells at a rate of 20000 cells/well. Five days later the cells were fixed with 4% paraformaldehyde and stained with violet crystal solution.

Figure 8:
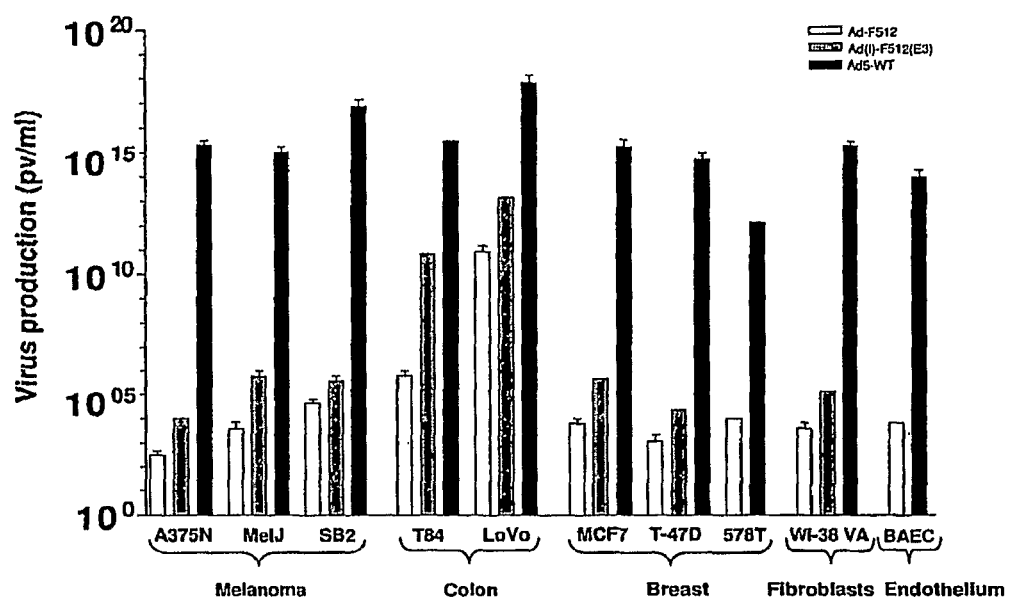
FIG. 8 shows the production of Ad-FS12 and Ad(I)-F512 (E3) adenoviruses of the present invention in different human tumor lines.

Referring to FIG. 8, the adenovirus yield in the different lines (melanoma, colon, breast, fibroblasts and endothelium) is expressed as viral particles per ml (vp/ml), and each bar represents the average of at least two independent assays.

In the first place, it can be pointed out that the adenovirus yield is independent of the SPARC mRNA expression. In the second place, all of the lines show greater Ad(I)-F512(E3) replication than that of Ad-F512 virus. In the third place, the Ad5-wt adenovirus yield differs among the different lines in a ratio of up to $10^5$ (e.g., comparing 578T to LoVo), what in part can be due to the low infectivity of some lines. Besides, the lines producing greater amounts of CRAds are those having greater susceptibility to CRAds (colon lines).

Example 13

Figure 9:
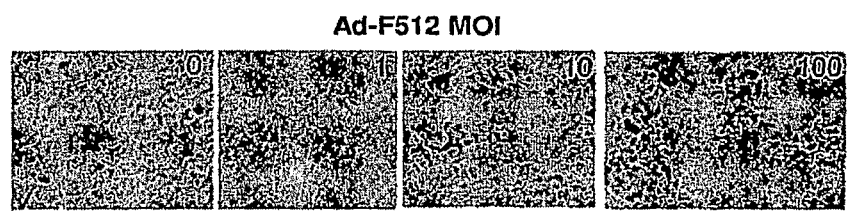
FIG. 9 shows the cooperative effect of the E1A gene given by Ad-F512 on the replication of the Ad-β-gal adenovirus.

Study on the Cooperative Effect Between Non-Replicative Viruses and Replicative Viruses As it was stated above, a non-replicative adenovirus requires the provision of the E1A protein in trans, so as to initiate replication. When an non-replicative adenovirus is amplified, they are used 293 cells that have been modified in order to constitutively express the E1A protein, but this protein can also be provided by a replicative adenovirus. In order to study the cooperation of Ad-F512 and a non-replicative adenovirus (Ad-β-gal), T84 colon cells were infected with a Constant amount of Ad-β-gal (MOI 10) and increasing amounts of Ad-F512. Ad-F512 is capable of complementing the non-replicative adenovirus, allowing its replication and distribution through neighbour cells, since as the Ad-F512 increases, an increase in the blue-stained cells is observed, denoting a local increase in Ad-β-gal virus. FIG. 9 shows the staining of βgal for the different assayed MOIs in T84 colon cells.

Example 14

In Vivo Assays Using Ad-F512 and Ad(I)-F512-TK CRAds 6-8 week-old Athymic male N:NIH(S)-nu mice (provided by the Veterinary College of the University of La Plata) were used for the assays. Three different in vivo assays were carried out using the recombinant adenoviruses obtained according to the present invention: two assays with Ad-F512 and one with Ad-(I)F512-TK.

Figure 10:
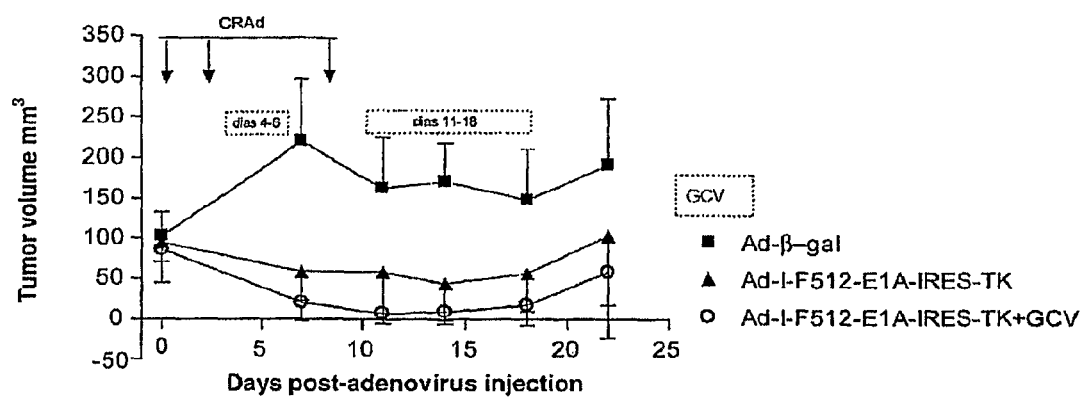
FIGS. 10A to 10F show the in vivo assay results.
Figure 10:
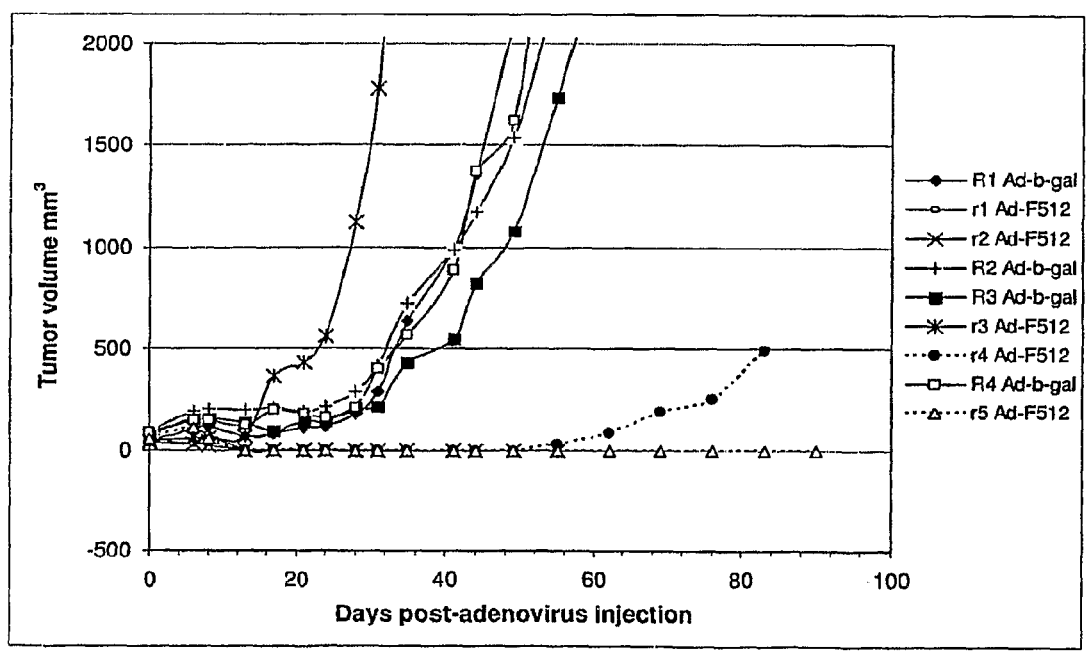
Figure 10:
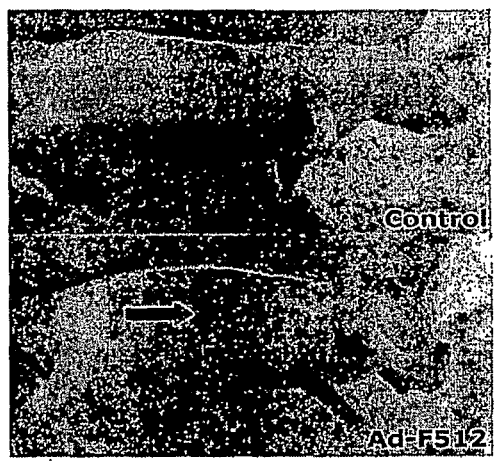
Figure 10:
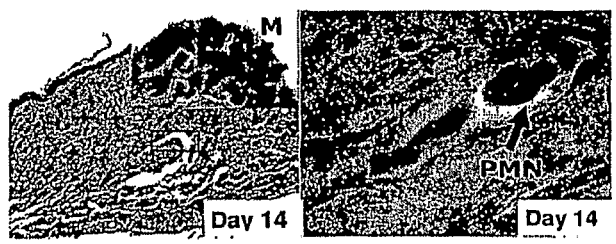
Figure 10:
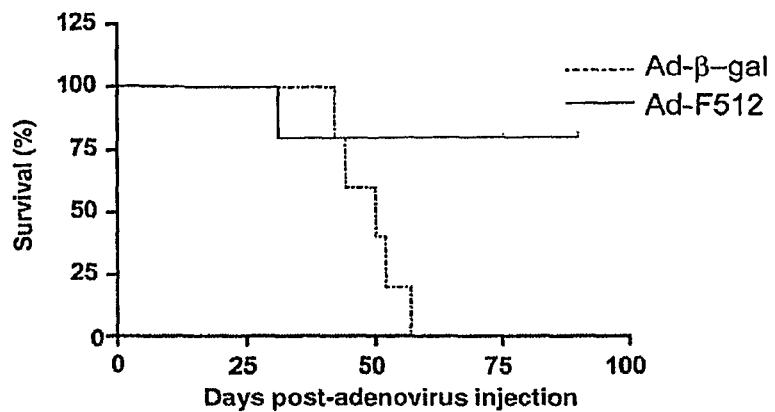
Figure 10:
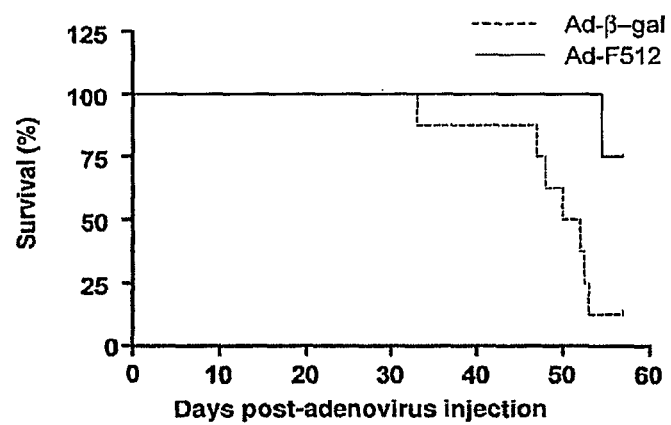

The animals were subcutaneously injected with an inoculum of $4 \times 10^6$ SB2 melanoma cells. When tumors reached a mean volume of 100 mm$^3$ (about 20 days after injection), the intratumoral injection of adenovirus started at $10^{10}$ vp/30 µl per dose. Each animal received three doses on days 0, 2 and 8 counting from the beginning of the treatment. In one of the assays, when using the CRAd expressing simultaneously the hsv-TK herpetic enzyme, the treatment with adenovirus was alternated with the injection of ganciclovir prodrug (GCV, Cytovene®, Rotang), according to what is shown in FIG. 10A, wherein the arrows indicate CRAd injections as well as the treatment with GCV. This drug was administered once a day at 30 mg/kg.

The control group received injections of an non-replicative adenovirus (Ad-β-gal), also expressing a non-therapeutic gene, instead of one of the two CRAds used in the present assay.

FIG. 10A shows the tumor growth curves in the assay using Ad-F512-TK. CRAd, wherein the administered CRAd injections and the ganciclovir administration are also indicated. FIG. 10B shows the curves of tumor growth in the mice used in the assay with Ad-F512. FIG. 10C is a photograph of the tumoral zone in a control mouse (injected with Ad-β-gal) and in one treated with Ad-F512 CRAd. FIG. 10D shows photographs of histological cuts made on some animals after 14 days from the beginning of the treatment. Finally, FIGS. 10E and 10F are Kaplan-Meier curves (survival %) for both assays realized with Ad-F512.

In both assays with Ad-F512 it was noted a total remission in most part of the treated tumors (FIGS. 10B, 10E and 10F) leaving a scar in the tumor site (shown by means of an arrow in FIG. 10C). Referring again to FIGS. 10E and 10F, these curves indicate that most part of the animals treated with Ad-F512 are still alive after 90 days, either because their tumors do not grow, they totally regress or they grow at a lower rate, while the control animals (tumor+Ad-β-gal) are dying because their tumors keep on growing.

Histological studies were carried out in some animals, by fixing in formaldehyde 10% and subsequent processing. This way, a histological study of the scar zone showed differences between days 14 and 90 counting from the beginning of the treatment: while on day 14 abundant macrophage infiltrate with pigments inside, with polymorphonuclear foci, nuclear remainings and granulomatose vascularization can be observed (see FIG. 10D), on day 90 it can be noted that the tissue has been repaired completely. In both cases an autopsy was carried out in the whole animal, not finding metastasis; however, on day 90 in one of the animals, the spleen with a fibrosis focus and the liver with a hepatitis focus were observed. None of the analyzed controls showed these characteristics.

The survival curves (FIGS. 10E and 10F) in both assays with Ad-F512 are very similar to each other and they are significantly different from the control.

Besides, referring to FIG. 10A, the assay with the CRAd expressing the suicide TK gene did not show statistically significant differences in the presence or in the absence of GCV, but the virus results equally effective compared to the control.

Example 15

Figure 11:
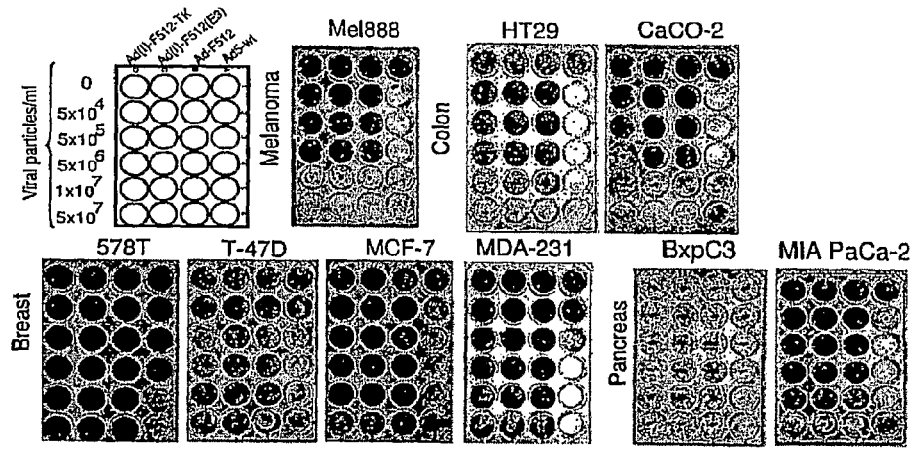
FIG. 11 shows the cytopathic effect in monolayer of Ad-F512, Ad(I)-F512-TK and Ad(I)-F512(E3) CRAds of the invention. The lytic effect (staining with violet crystal) of the CRAds in cell monolayers at different concentrations after 10 days post-infection is shown.

In Vitro Assays Using Ad-F512, Ad(I)-F512-TK and Ad(I)-F512(E3) CRAds a) Analysis of Tumor Lines In this step, the previous analysis carried out as described in Example 11 was extended by testing other tumor lines of melanoma, colon, breast and pancreas cancers. The cytopathic effect of viruses on the cells was analyzed by staining with violet crystal the cells that remained attached to the well after 10 days post-infection with the adenovirus. The results are shown in FIG. 11.

The Mel888 melanoma cells (kindly provided by Dr. Estela Medrano, Houston, Tex.) were lysed by the adenoviruses at same viral concentrations than for the assays with SB2 and IIB-Mel-J cells (the former kindly provided by Dr. Estela Medrano, Houston, Tex. and the latter by Ledda et al., *Suppression of SPARC expression by antisense RNA abrogates the tumorigenicity of human melanoma cells*. Nat Med. 1997 February; 3(2):171-6) tested in Example 11 above. The two colon lines HT29 (ATTC No. HTB-38) and CaCO-2 (ATCC No. HTB-37) included in these new assays also show the susceptibility of colon cells to the constructed CRAds. It has been found that the MIA-PaCa-2 pancreas cancer line (ATCC No. CRL-1420) is sensitive to a $5 \times 10^7$ vp/ml adenovirus concentration, while the four analyzed 578T breast lines (ATCC No. HTB-126), T-47D (ATCC No. HTB-133), MCF-7 (ATCC No. HTB-22) and MDA-231 (ATCC No. HTB-26) are not affected by CRAds, (see FIG. 11). In all cases, the wild type virus (AD5-wt) is capable of eliminating all tumor cells.

b) Analysis of Normal Lines

Figure 12:
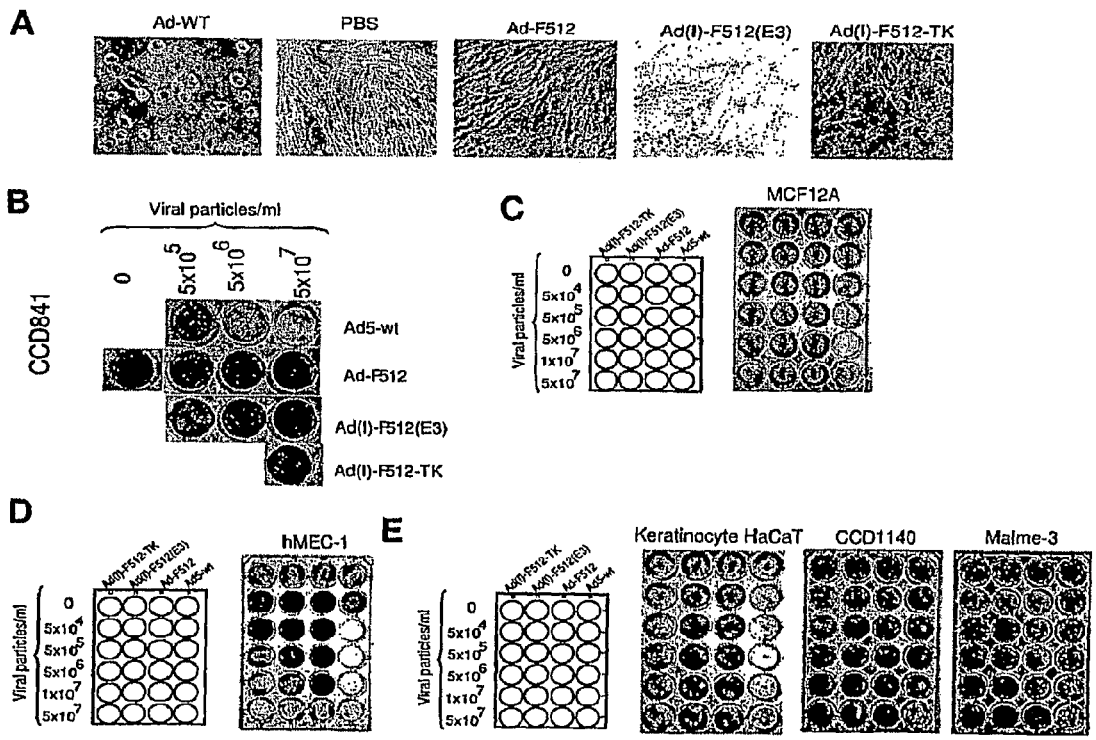
FIGS. 12A to 12E show the cytopathic effect of Ad-F512, Ad(I)-F512-TK and AD(I)-F512(E3) CRAds of the invention, in normal cells.

One of the requirements for using an oncolytic adenovirus in a clinical assay is that it should be active in tumor cells and inactive in normal cells. In order to establish the attenuation level in normal cells of the three constructed oncolytic viruses, their activity was analyzed in a panel of said cells. Normal melanocyte, colon and breast cell lines were included as well as fibroblasts, keratinocytes and human microendothelial cells. After 10 days post-infection with $5 \times 10^6$ viral particles/ml of Ad-F512, Ad(I)-Fs12-TK or Ad(I)-F512(E3) the viability of melanocytes was greater than 95% while 100% of cells were lysed by the Ad-wt (see FIG. 12A). It was shown (see FIG. 12B) that the oncolytic viruses also had no effect on normal CCD841 colon cells (ATCC No. CRL-1790) and normal MCF-12A breast cells (ATCC No. CRL-10782) (see FIG. 12C). These lines have no SPARC expression (see Table 3 below). hMEC-1 human microendothelial cells were also analyzed (kindly provided by Isaiah Fidler, Houston, Tex.) with SPARC expression and it was noted that they are lysed by the adenoviruses at a high MOI (see FIG. 12D). Subsequently other cell components present in the skin, like keratinocytes or fibroblasts were analyzed. The former do not produce SPARC while the latter have an intermediate SPARC expression when compared to A375N tumor cell line (see Table 3 below). The viral effect on keratinocytes (HaCaT, kindly provided by Craveri Laboratory), on CCD1140 fibroblast cells (ATCC No. CRL-2714) and on Malme-3 (ATCC No. HTB-102) is shown in FIG. 12E. It was noted that neither the keratinocytes nor the fibroblast lines were lysed by the adenoviruses.

Therefore, CRAds do not lyse normal cells which do not express SPARC (colon, breast, melanocytes, keratinocytes,), lysing, instead, hMEC-1 microendothelial cells which do express SPARC.

TABLE 3

Relative SPARC expression of the cell lines used in the study.

| Cell line | Origin | Average | SD |
|---|---|---|---|
| A375N | Melanoma | 1 | 0 |
| Mel888 | Melanoma | 0.1523333 | 0.00617342 |
| HT-29 | Colon | 0.00083554 | 1.4217E−05 |
| CaCO2 | Colon | 0.00194873 | 0.00047591 |
| 578T | Breast | 1.585 | 0.345 |
| T-47D | Breast | 0.00152448 | 0.00045275 |
| MCF-7 | Breast | 0 | 0 |
| MDA-231 | Breast | 0 | 0 |
| BxPC3 | Pancreas | 0 | 0 |
| MiaPaca-2 | Pancreas | 0 | 0 |
| NHM | Normal melanocytes | 0.05 | 0 |
| CCD841 | Normal colon | 0.04033333 | 0.01125956 |
| MCF12-A | Normal breast | 0 | 0 |
| hMEC-1 | microendothelial | 0.20225 | 0.01271728 |
| HACAT | keratinocytes | 0.0005 | 0.0005 |
| CCD1140 | fibroblasts | 0.417 | 0.0609836 |

Figure 13:
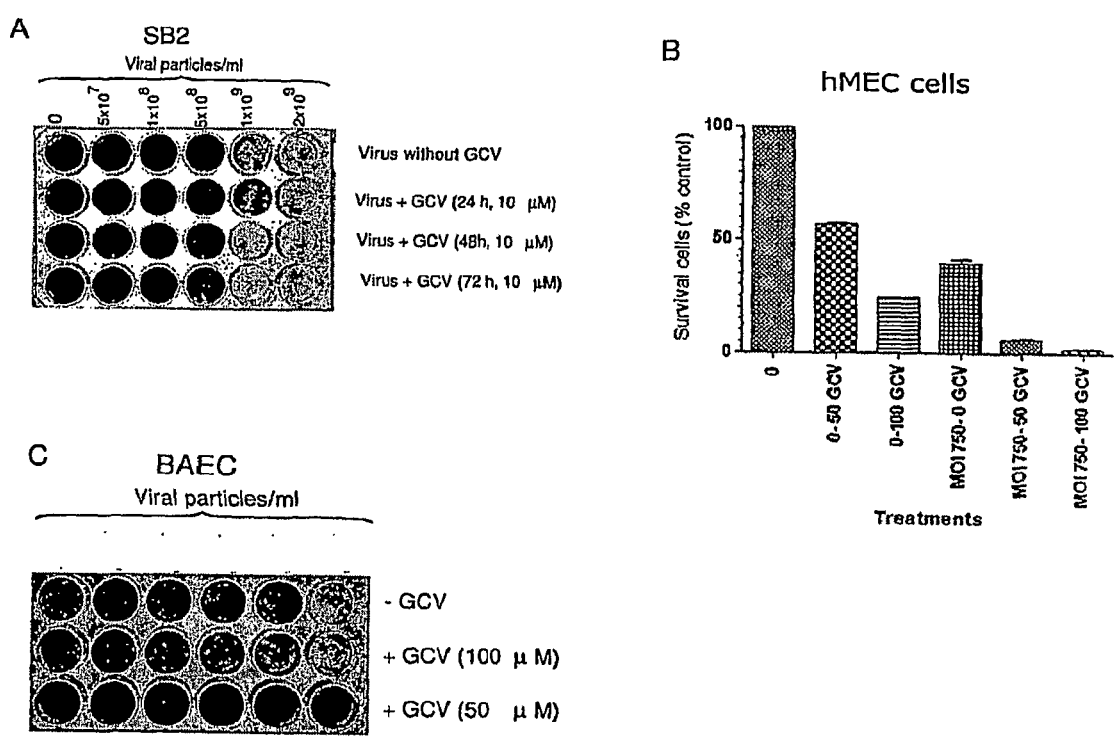
FIGS. 13A to 13C show the monolayer cytopathic effect of Ad(I)-F512-TK; the lytic effect (staining with violet crystal or survival measured by MTT) of Ad(I)-F512-TK on monolayers of cells at different viral concentrations after 10 days post-infection in the presence or absence of GCV prodrug.

The average SPARC mRNA expression is shown in relation to the A375N tumoral line expression.
SD: Standard deviation.

c) Ad(I)-F512-TK Lytic Effect in Cells Expressing SPARC: Tumoral and Stromal Cells (Fibroblasts and Endothelium) Growing in Monolayer In vitro assays with tumoral stromal cells (endothelial and fibroblasts) showed that even with high or moderated SPARC expression the adenoviruses did not have the same activity as in tumor cells. According to the present inventors' hypothesis, normal cells have more resistance to viral replication. In this case, adding a toxic gene would allow for the enhancement of the lytic capability in a specific manner in those cells wherein the SPARC promoter was active. Thus, in vitro assays with Ad(I)-F512-TK were carried out, in which the cells were also treated by adding ganciclovir (GCV) prodrug. In the first place, it was noted that adding GCV improves virus lysis in SB2 melanoma cells (see FIG. 13A); this improvement is more effective if the addition of GCV starts 72 hs after the beginning of the oncolytic virus action. Regarding endothelial cells, they are sensitive to the presence of the prodrug alone (see in FIG. 13B the first three bars on the left). Adding the virus at a MOI of 750 and in presence of CGV 50 μM or 100 μM allows for the elimination of almost all of the cells (last two columns in FIG. 13B). Other analyzed endothelial cells were those of bovine aorta (BAEC, kindly provided by Helene Sage, Seattle, USA). However, these cells which express higher SPARC values than A375N and in which the F512 human promoter is very active (see Examples 1 and 3B above), do not get properly infected with the Ad5 capsid. Similarly to hMEC-1, the cells are sensitive to the prodrug, but the presence of the GCV prodrug in addition to the virus allows for the elimination of cells at viral concentrations in which the virus itself has no effect (see FIG. 13C).

Example 16

In Vivo Assays Using Ad-F512 and Ad(I)-F512-TK CRAds

In vivo assays were carried out in animals (6-8 week-old athymic male mice N:NIH(S)-nu), that were injected with mixed melanoma tumors comprising tumoral and stromal cells. Subsequently, these tumors were treated with the CRAds obtained according to the present invention, using the same protocol than that for tumors of only melanoma cells.

Figure 14:
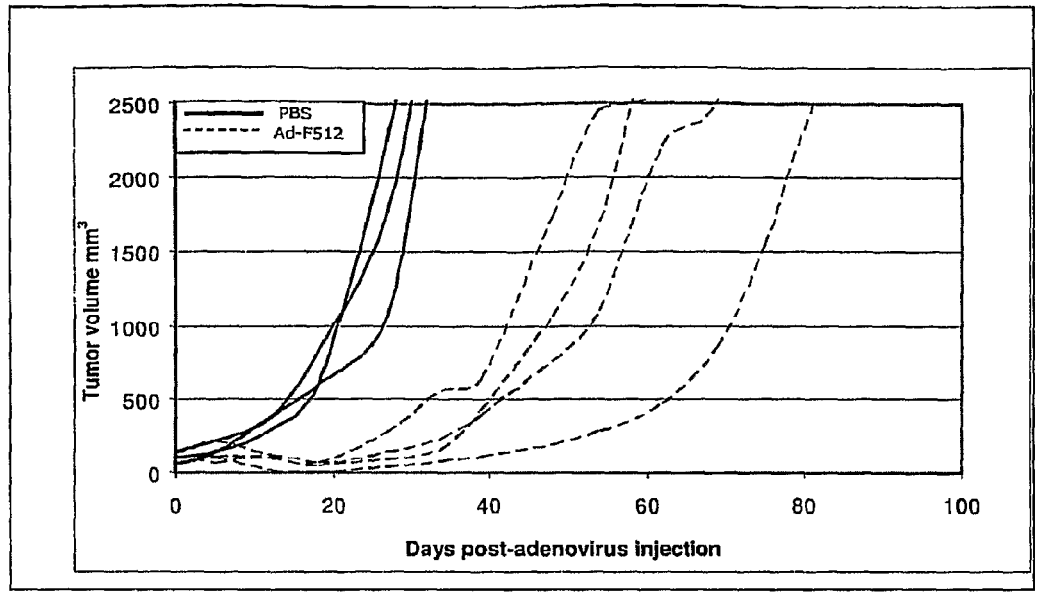
FIGS. 14A to 14D show in vivo assays with melanoma tumors.
Figure 14:
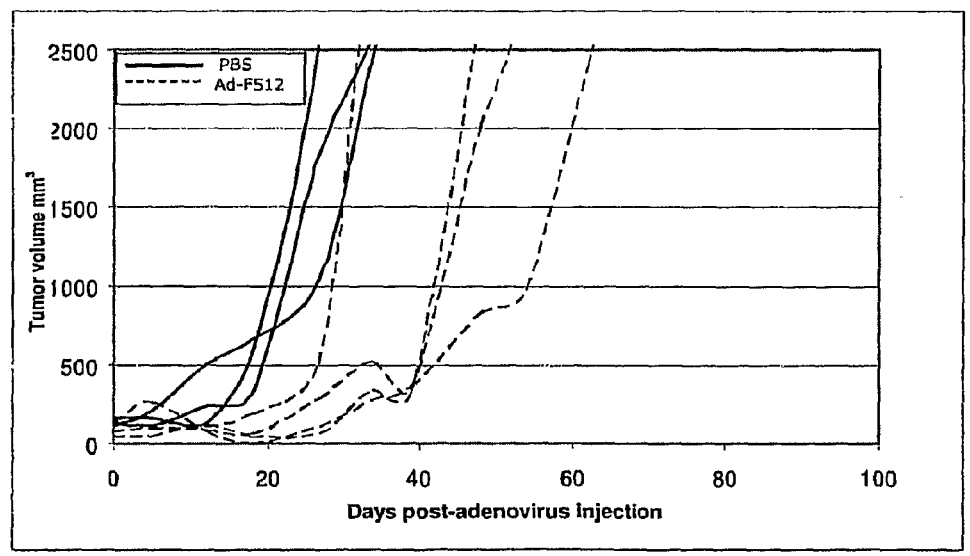
Figure 14:
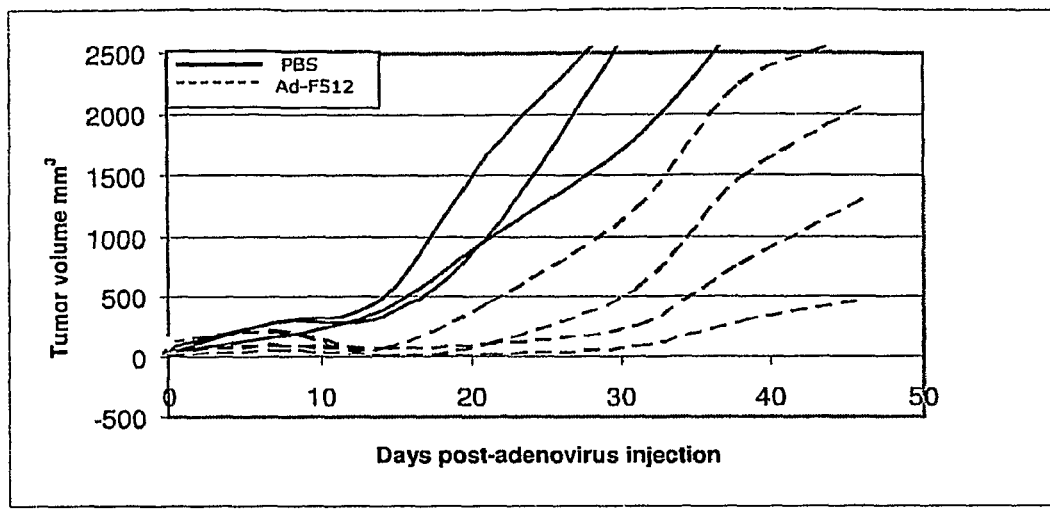
Figure 14:
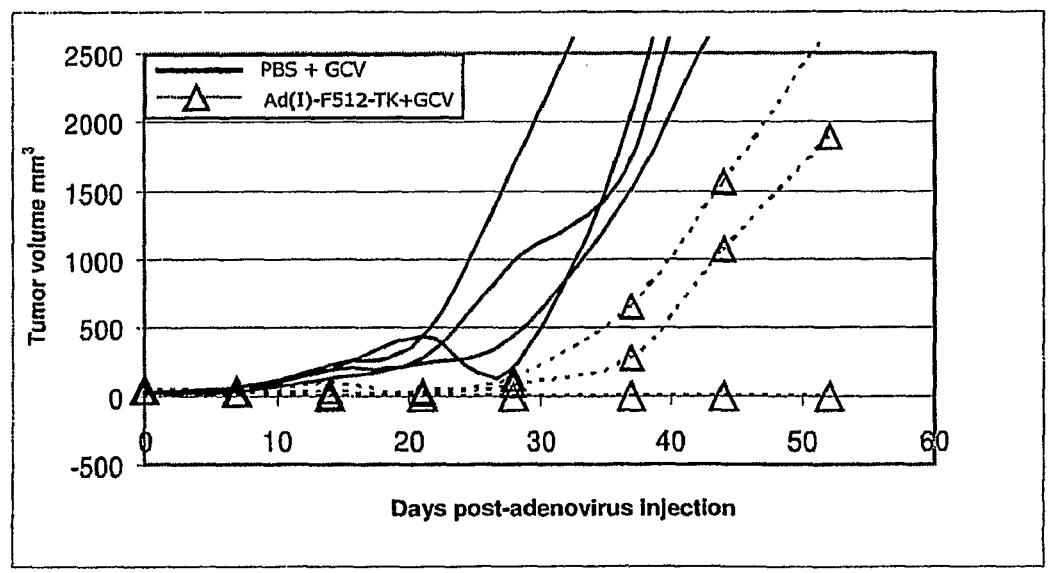

FIG. 14A shows the results of an assay in which animals carried SB2/hMEC-1/WI-38 mixed tumors and were treated with Ad-F512. It was noted that treatment with the adenovirus produces a relevant delay in growth tumor, even when the malignant cells were co-injected with endothelial cells (hMEC-1) and fibroblasts (WI-38), showing that this virus can be effective, in a similar situation occurring in a tumor.

The same result was obtained when repeating the assay (data not shown).

It was also assessed the efficacy of the adenoviral treatment on mixed tumors of tumoral cells and fibroblasts. It was noted that the treatment of SB2/WI38 tumors with Ad-F512 resulted partially effective (FIG. 14B). When SB2/hMEC-1 cells were injected, it was noted that some of the animals responded much better to the treatment, even though there were no rejections (FIG. 14C). Finally, SB2/WI-38 tumors were treated with Ad(I)-F512-TK+GCV, noting that 3 animals of a total of 5 animals completely rejected the tumor, indicating that the addition of the TK toxic gene significantly improves the virus effect (FIG. 14D).

Besides, it has been disclosed (Yamazaki, M., Straus, F. H., Messina, M., Robinson, B. G., Takeda, T., Hashizume, K., and DeGroot, L. J. *Adenovirus-mediated tumor-specific combined gene therapy using Herpes simplex virus thymidine/ganciclovir system and murine interleukin-12 induces effective antitumor activity against medullary thyroid carcinoma*. Cancer Gene Ther, 11: 8-15, 2004. ) that many CRAds show greater unspecificity in vitro than in vivo. As disclosed in Example 11, the viruses of the present invention were able to eliminate colon cancer cells in vitro. However, previous studies (Yamazaki et al., 2004, above) suggested that this could be due to unspecific effects. Therefore, in vivo assays with colon and pancreas cancer tumors were carried out.

A remarkable in vivo effect on colon tumors was noted. In fact, Ad-F512 and Ad(I)-F512-TK were not able to eliminate in vivo the LoVo cell tumor (FIG. 15A); however, the addition of hMEC-1 endothelial cells to those tumors and in the presence of GCV allowed for the delay in the colon tumor growth, compared to the tumors of the control group, indicating that the presence of endothelial cells expressing SPARC could enhance the elimination of tumors the malignant cells of which do not express SPARC (FIG. 15B).

Figure 15:
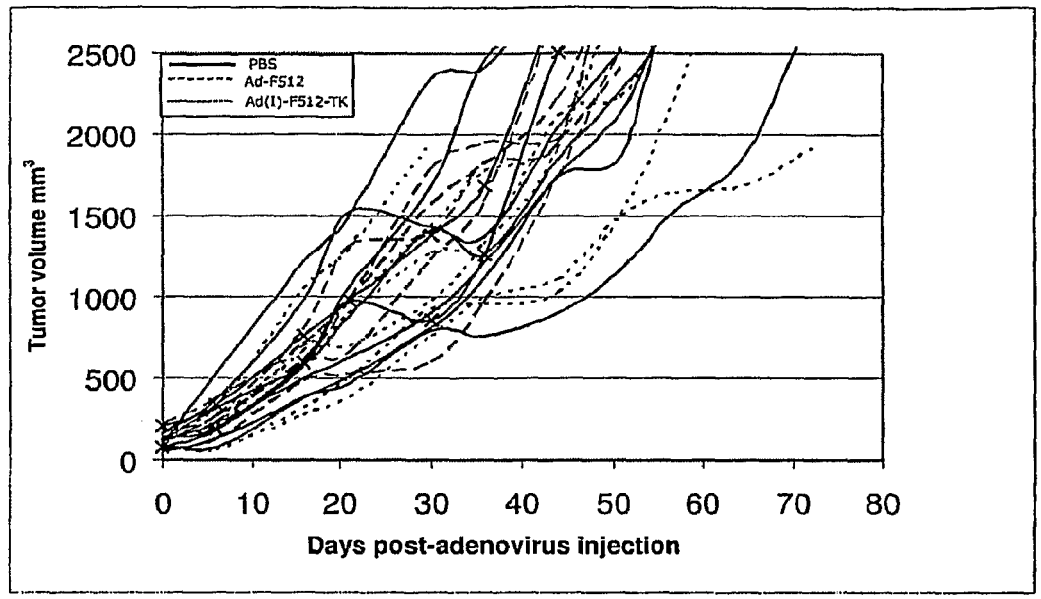
FIGS. 15A to 15D show in vivo assays with colon and pancreas tumors.
Figure 15:
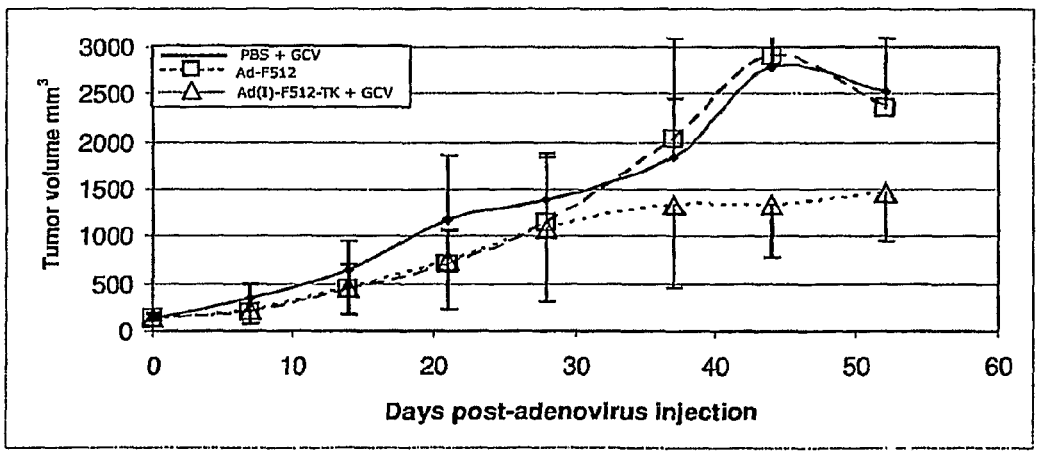
Figure 15:
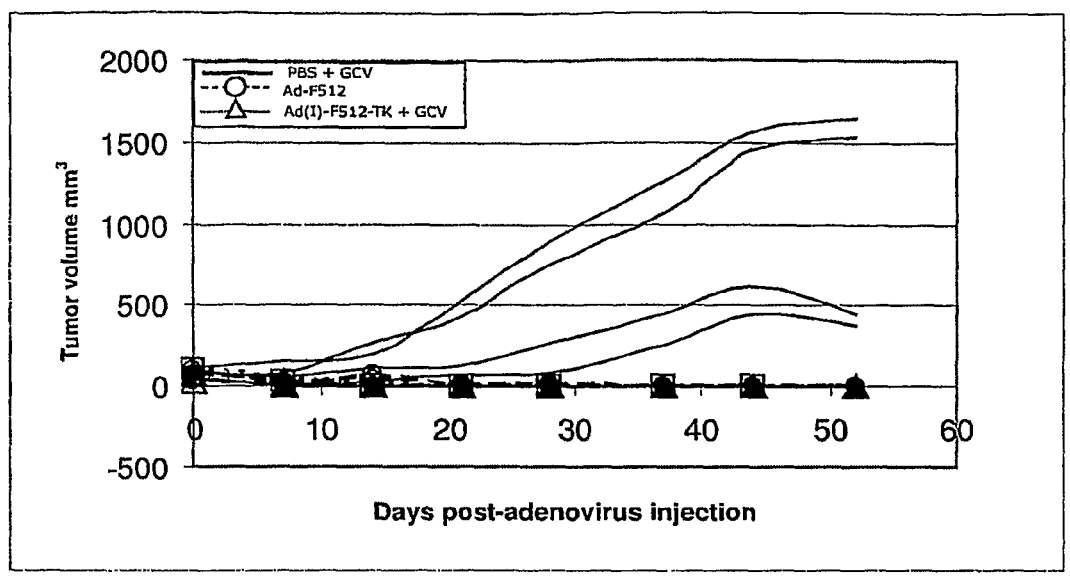

On the same basis, in another group of experiments, Mia-PaCa-2 (ATCC No. CRL-1420) (malignant, pancreas)/hMEC-1 mixed tumors were treated with Ad-Fs12 and Ad(I)-F512-TK+GCV, showing, surprisingly, that these tumors are completely eliminated (FIG. 15C).

While the illustrated embodiments of the invention disclosed herein, fulfill the objects of the present invention, many modifications and other embodiments may be apparent for a person skilled in the art. Therefore, it shall be understood that the annexed claims are intended to encompass all of said modifications and embodiments, that will be within the spirit and scope of the present invention.

The invention claimed is:

1. An isolated DNA comprising a single fragment of the human SPARC promoter, said single fragment being of SEQ ID NO: 1.

2. The isolated DNA of claim 1, wherein the single fragment of the human SPARC promoter is operably linked to a heterologous gene.

3. The isolated DNA of claim 1, further comprising a regulating sequence selected from a radiation responsive sequence, a hypoxia responsive sequence or a free-radical responsive sequence.

4. The isolated DNA of claim 2, wherein the heterologous gene is a therapeutic gene.

5. The isolated DNA of claim 2, wherein the heterologous gene is an E1A gene.

6. The isolated DNA of claim 2, wherein the isolated DNA sequence is an expression vector.

7. The expression vector of claim 6, wherein the vector is a viral vector.

8. The expression vector of claim 7, wherein the viral vector is a recombinant adenovirus.

9. The expression vector of claim 8, wherein the viral vector is a Conditionally Replicative Oncolytic Adenovirus.

10. The expression vector of claim 6, wherein the heterologous gene is a therapeutic gene.

11. The expression vector of claim 10, wherein the therapeutic heterologous gene is an E1A protein gene.

12. A pharmaceutical composition comprising the expression vector of claim 6 in a pharmaceutically suitable carrier.

13. An expression vector comprising a single fragment of the human SPARC promoter, said single fragment being of SEQ ID NO: 1.

\* \* \* \* \*